United States Patent
Piferi

(10) Patent No.: US 9,891,296 B2
(45) Date of Patent: Feb. 13, 2018

(54) INTRABODY FLUID TRANSFER DEVICES, SYSTEMS AND METHODS

(71) Applicant: MRI Interventions, Inc., Memphis, TN (US)

(72) Inventor: Peter Piferi, Orange, CA (US)

(73) Assignee: MRI Interventions, Inc., Irvine, CA (US)

( * ) Notice: Subject to any disclaimer, the term of this patent is extended or adjusted under 35 U.S.C. 154(b) by 675 days.

(21) Appl. No.: 14/468,922

(22) Filed: Aug. 26, 2014

(65) Prior Publication Data

US 2015/0080708 A1    Mar. 19, 2015

Related U.S. Application Data

(60) Provisional application No. 61/877,451, filed on Sep. 13, 2013.

(51) Int. Cl.
   *G01R 33/28*    (2006.01)
   *A61M 5/158*    (2006.01)
   (Continued)

(52) U.S. Cl.
   CPC ........ *G01R 33/286* (2013.01); *A61B 10/0233* (2013.01); *A61M 5/158* (2013.01);
   (Continued)

(58) Field of Classification Search
   CPC ................ G01R 33/286; G01R 33/287; G01R 33/34084; A61B 10/0233; A61B 5/055;
   (Continued)

(56) References Cited

U.S. PATENT DOCUMENTS 3,352,306 A * 11/1967 Hrisch ............. A61M 25/0606
                                                    604/164.01
3,540,447 A * 11/1970 Howe ................ A61B 17/3401
                                                    604/165.02
(Continued)

FOREIGN PATENT DOCUMENTS

EP    1 334 740 A1    8/2003
EP    1 482 851 A1    12/2004
(Continued)

OTHER PUBLICATIONS

Bankiewicz et al. "Convection-Enhanced Delivery of AAV Vector in Parkinsonian Monkeys; In Vivo Detection of Gene Expression and Restoration of Dopaminergic Function Using Pro-drug Approach" *Experimental Neurology* 164:2-14 (2000).
(Continued)

*Primary Examiner* — Manuel Mendez
(74) *Attorney, Agent, or Firm* — Myers Bigel, P.A.

(57) ABSTRACT

Devices, kits, assemblies systems and methods for transferring fluid to or from a subject include an elongate guide cannula having opposing proximal and distal ends with an open axially extending lumen. The proximal end includes a connector. The devices also include an elongate needle having opposing proximal and distal ends, the needle having a connector that is configured to attach to the guide cannula connector and is attached to or attachable to a length of flexible tubing, wherein the elongate needle is configured to be slidably inserted into the guide cannula lumen so that the distal end of the needle extends out of the distal end of the distal end of the guide cannula a suitable distance.

24 Claims, 16 Drawing Sheets

(51) Int. Cl.
*A61B 10/02* (2006.01)
*A61B 5/055* (2006.01)
*G01R 33/34* (2006.01)
*A61M 39/02* (2006.01)

(52) U.S. Cl.
CPC ........ *A61B 5/055* (2013.01); *A61M 2039/025* (2013.01); *A61M 2205/0211* (2013.01); *A61M 2205/0227* (2013.01); *A61M 2210/0687* (2013.01); *A61M 2210/0693* (2013.01); *G01R 33/287* (2013.01); *G01R 33/34084* (2013.01)

(58) Field of Classification Search
CPC ............ A61M 5/158; A61M 2039/025; A61M 2210/0693; A61M 2205/0211; A61M 2205/0227; A61M 2210/0687
USPC .... 604/164.01–164.02, 165.01–165.02, 158, 604/272, 110, 506, 513, 167.04, 166.01
See application file for complete search history.

(56) References Cited

U.S. PATENT DOCUMENTS

| | | | |
|---|---|---|---|
| 3,856,009 A | 12/1974 | Winnie | |
| 4,149,535 A | 4/1979 | Volder | |
| 4,239,042 A | 12/1980 | Asai | |
| 4,265,928 A | 5/1981 | Braun | |
| 4,327,722 A | 5/1982 | Groshong et al. | |
| 4,449,532 A | 5/1984 | Storz | |
| 4,531,943 A | 7/1985 | Van Tassel et al. | |
| 4,543,091 A | 9/1985 | Froning et al. | |
| 4,543,092 A | 9/1985 | Mehler et al. | |
| 4,597,421 A | 7/1986 | Wells | |
| 4,623,789 A | 11/1986 | Ikeda et al. | |
| 4,629,450 A | 12/1986 | Suzuki et al. | |
| 4,705,511 A * | 11/1987 | Kocak ................. | A61M 25/005 604/167.04 |
| 4,738,658 A | 4/1988 | Magro et al. | |
| 4,739,768 A | 4/1988 | Engelson | |
| 4,781,691 A | 11/1988 | Gross | |
| 4,846,799 A | 7/1989 | Tanaka et al. | |
| 4,897,077 A | 1/1990 | Cicciu et al. | |
| 4,955,863 A | 9/1990 | Walker et al. | |
| 4,978,334 A | 12/1990 | Toye et al. | |
| 4,995,866 A * | 2/1991 | Amplatz ............. | A61M 5/3286 604/166.01 |
| 5,069,673 A | 12/1991 | Shwab | |
| 5,380,292 A | 1/1995 | Wilson | |
| 5,562,626 A | 10/1996 | Sanpietro | |
| 5,699,801 A | 12/1997 | Atalar et al. | |
| 5,720,720 A | 2/1998 | Laske et al. | |
| 5,792,144 A | 8/1998 | Fischell et al. | |
| 5,833,662 A * | 11/1998 | Stevens ............. | A61M 39/0606 600/573 |
| 5,851,203 A | 12/1998 | van Muiden | |
| 5,871,470 A * | 2/1999 | McWha ............. | A61B 17/3401 604/158 |
| 5,902,282 A | 5/1999 | Balbierz | |
| 5,919,171 A | 7/1999 | Kira et al. | |
| 5,928,145 A | 7/1999 | Ocali et al. | |
| 6,020,196 A | 2/2000 | Hu et al. | |
| 6,026,316 A | 2/2000 | Kucharczyk et al. | |
| 6,030,369 A | 2/2000 | Engelson et al. | |
| 6,042,579 A | 3/2000 | Elsberry et al. | |
| 6,050,992 A | 4/2000 | Nichols | |
| 6,093,180 A | 7/2000 | Elsberry | |
| 6,167,311 A | 12/2000 | Rezai | |
| 6,186,986 B1 | 2/2001 | Berg et al. | |
| 6,263,229 B1 | 7/2001 | Atalar et al. | |
| 6,284,971 B1 | 9/2001 | Atalar et al. | |
| RE37,410 E | 10/2001 | Brem et al. | |
| 6,309,634 B1 | 10/2001 | Bankiewicz et al. | |
| 6,336,915 B1 | 1/2002 | Scarfone et al. | |
| 6,356,786 B1 | 3/2002 | Rezai et al. | |
| 6,405,079 B1 | 6/2002 | Ansarinia | |
| 6,438,423 B1 | 8/2002 | Rezai et al. | |
| 6,524,299 B1 | 2/2003 | Tran et al. | |
| 6,526,318 B1 | 2/2003 | Ansarinia | |
| 6,533,751 B2 | 3/2003 | Cragg et al. | |
| 6,539,263 B1 | 3/2003 | Schiff et al. | |
| 6,551,290 B1 | 4/2003 | Elsberry et al. | |
| 6,585,694 B1 | 7/2003 | Smith et al. | |
| 6,606,513 B2 | 8/2003 | Lardo et al. | |
| 6,609,030 B1 | 8/2003 | Rezai et al. | |
| 6,628,980 B2 | 9/2003 | Atalar et al. | |
| 6,641,555 B1 * | 11/2003 | Botich ................. | A61M 5/158 604/110 |
| 6,641,564 B1 | 11/2003 | Kraus | |
| 6,675,033 B1 | 1/2004 | Lardo et al. | |
| 6,701,176 B1 | 3/2004 | Halperin et al. | |
| 6,708,064 B2 | 3/2004 | Rezai | |
| 6,904,307 B2 | 6/2005 | Karmarkar et al. | |
| 7,037,295 B2 | 5/2006 | Tiernan et al. | |
| 7,182,944 B2 | 2/2007 | Bankiewicz | |
| 7,329,262 B2 | 2/2008 | Gill | |
| 7,341,577 B2 | 3/2008 | Gill | |
| 7,351,239 B2 | 4/2008 | Gill | |
| 7,371,225 B2 | 5/2008 | Oldfield et al. | |
| 7,780,692 B2 | 8/2010 | Nance et al. | |
| 7,815,623 B2 | 10/2010 | Bankiewicz et al. | |
| 7,892,203 B2 | 2/2011 | Lenker et al. | |
| 7,951,110 B2 | 5/2011 | Bishop et al. | |
| 8,128,600 B2 | 3/2012 | Gill | |
| 8,175,677 B2 | 5/2012 | Sayler et al. | |
| 8,195,272 B2 | 6/2012 | Piferi et al. | |
| 8,315,689 B2 | 11/2012 | Jenkins et al. | |
| 8,340,743 B2 | 12/2012 | Jenkins et al. | |
| 8,348,892 B2 | 1/2013 | Lenker et al. | |
| 8,374,677 B2 | 2/2013 | Piferi et al. | |
| 8,597,277 B2 | 12/2013 | Lenker et al. | |
| 8,827,987 B2 | 9/2014 | Fielder et al. | |
| 8,900,214 B2 | 12/2014 | Nance et al. | |
| 9,044,577 B2 | 6/2015 | Bishop et al. | |
| 9,050,419 B2 | 6/2015 | Farnan | |
| 9,452,241 B2 | 9/2016 | Gill et al. | |
| 2002/0087152 A1 | 7/2002 | Mikus et al. | |
| 2002/0091372 A1 | 7/2002 | Cragg et al. | |
| 2002/0095081 A1 | 7/2002 | Vilsmeier | |
| 2002/0114780 A1 | 8/2002 | Bankiewicz et al. | |
| 2002/0141980 A1 | 10/2002 | Bankiewicz et al. | |
| 2002/0183763 A1 | 12/2002 | Callol et al. | |
| 2003/0028095 A1 | 2/2003 | Tulley et al. | |
| 2003/0050557 A1 | 3/2003 | Susil et al. | |
| 2003/0073934 A1 | 4/2003 | Putz | |
| 2003/0216714 A1 | 11/2003 | Gill | |
| 2004/0046557 A1 | 3/2004 | Karmarkar et al. | |
| 2004/0092879 A1 | 5/2004 | Kraus et al. | |
| 2004/0199129 A1 | 10/2004 | DiMatteo | |
| 2004/0209810 A1 | 10/2004 | Gill et al. | |
| 2004/0215162 A1 | 10/2004 | Putz | |
| 2004/0249261 A1 | 12/2004 | Torchia et al. | |
| 2005/0004504 A1 | 1/2005 | Frye et al. | |
| 2005/0112065 A1 | 5/2005 | Drummond et al. | |
| 2005/0148865 A1 | 7/2005 | Weber | |
| 2005/0154297 A1 | 7/2005 | Gill | |
| 2005/0256503 A1 | 11/2005 | Hall | |
| 2006/0052750 A1 | 3/2006 | Lenker et al. | |
| 2006/0073101 A1 | 4/2006 | Oldfield et al. | |
| 2006/0129126 A1 | 6/2006 | Kaplitt et al. | |
| 2006/0135945 A1 | 6/2006 | Bankiewicz et al. | |
| 2006/0217664 A1 | 9/2006 | Hattler et al. | |
| 2007/0088295 A1 | 4/2007 | Bankiewicz | |
| 2007/0110798 A1 | 5/2007 | Drummond et al. | |
| 2007/0179455 A1 * | 8/2007 | Geliebter .............. | A61M 5/329 604/272 |
| 2007/0250021 A1 | 10/2007 | Brimhall et al. | |
| 2007/0254842 A1 | 11/2007 | Bankiewicz | |
| 2008/0119821 A1 * | 5/2008 | Agnihotri ............. | A61B 10/025 604/513 |
| 2008/0228168 A1 | 9/2008 | Mittermeyer et al. | |
| 2009/0088695 A1 | 4/2009 | Kapur et al. | |
| 2009/0088730 A1 | 4/2009 | Hoofnagle et al. | |
| 2009/0112084 A1 | 4/2009 | Piferi et al. | |

(56) References Cited

U.S. PATENT DOCUMENTS

| | | | |
|---|---|---|---|
| 2009/0118610 A1 | 5/2009 | Karmarkar et al. | |
| 2009/0143764 A1 | 6/2009 | Nelson | |
| 2009/0171184 A1 | 7/2009 | Jenkins et al. | |
| 2009/0198218 A1 | 8/2009 | Gill et al. | |
| 2009/0209937 A1 | 8/2009 | Rogawski et al. | |
| 2009/0281453 A1 | 11/2009 | Tsonton et al. | |
| 2010/0130958 A1* | 5/2010 | Kang | A61M 5/158 604/506 |
| 2010/0198052 A1 | 8/2010 | Jenkins et al. | |
| 2010/0217236 A1 | 8/2010 | Gill et al. | |
| 2010/0318061 A1 | 12/2010 | Derrick et al. | |
| 2010/0318064 A1 | 12/2010 | Derrick et al. | |
| 2011/0282319 A1 | 11/2011 | Gill | |
| 2012/0123391 A1 | 5/2012 | Gill et al. | |
| 2012/0310182 A1 | 12/2012 | Fielder et al. | |
| 2013/0030408 A1 | 1/2013 | Piferi et al. | |
| 2014/0257168 A1 | 9/2014 | Gill | |
| 2014/0343500 A1 | 11/2014 | Fielder et al. | |
| 2016/0346505 A1 | 12/2016 | Gill et al. | |

FOREIGN PATENT DOCUMENTS

| | | |
|---|---|---|
| EP | 1 491 154 A1 | 12/2004 |
| GB | 1 255 551 | 12/1971 |
| JP | 2002-509767 A | 4/2002 |
| JP | 2004-147830 A | 5/2004 |
| WO | WO 99/04849 A1 | 2/1999 |
| WO | WO 99/49909 A2 | 10/1999 |
| WO | WO 02/053205 A2 | 7/2002 |
| WO | WO 03/077785 A1 | 9/2003 |
| WO | WO 2004/031348 A2 | 4/2004 |
| WO | WO 2008/020237 A2 | 2/2008 |
| WO | WO 2008/020241 A2 | 2/2008 |
| WO | WO 2008/144585 A1 | 11/2008 |
| WO | WO 2008/144775 A1 | 11/2008 |
| WO | WO 2009/042135 A2 | 4/2009 |
| WO | WO 2009/047490 A2 | 4/2009 |
| WO | WO 2009/066130 A1 | 5/2009 |
| WO | WO 2009/101397 A1 | 8/2009 |
| WO | WO 2010/040970 A2 | 4/2010 |
| WO | WO 2011/098768 A1 | 8/2011 |
| WO | WO 2011/098769 A1 | 8/2011 |
| WO | WO 2012/178169 A2 | 12/2012 |
| WO | WO 2013/050148 A1 | 4/2013 |
| WO | WO 2014/089373 A1 | 6/2014 |

OTHER PUBLICATIONS

Chen et al. "Variables affecting convection-enhanced delivery to the striatum: a systematic examination of rate of infusion, cannula size, infusate concentration, and tissue-cannula sealing time" *Journal of Neurosurgery* 90:315-320 (1999).

Chen et al. "Combination Therapy with Irinotecan and Protein Kinase C Inhibitors in Malignant Glioma" *Cancer* 97(9 Suppl):2363-2373 (2003).

Chen et al. "Surface properties, more than size, limiting convective distribution of virus-sized particles and viruses in the central nervous system" *Journal of Neurosurgery* 103:311-319 (2005).

Cunningham et al. "Distribution of AAV-TK following intracranial convection-enhanced delivery into rats" *Cell Transplantation* 9(5):585-594 (2000) (Abstract Only).

Groothuis, Dennis R. "The blood-brain and blood-tumor barriers: A review of strategies for increasing drug delivery" *Neuro-Oncology* 2:45-59 (2000).

Hadaczek et al. "Convection-Enhanced Delivery of Adeno-Associated Virus Type 2 (AAV2) into the Striatum and Transport of AAV2 Within Monkey Brain" *Human Gene Therapy* 17:291-302 (2006).

Hadaczek et al. "The 'Perivascular Pump' Driven by Arterial Pulsation is a Powerful Mechanism for the Distribution of Therapeutic molecules within the Brain" *Molecular Therapy* 14(1):69-78 (2006).

Krauze et al. "Reflux-free cannula for convection-enhanced high-speed delivery of therapeutic agents" *Journal of Neurosurgery* 103:923-929 (2005).

Krauze et al. "Real-time Imaging and Quantification of Brain Delivery of Liposomes" *Pharmaceutical Research* 23(11):2493-2504 (2006).

Laske et al. "Chronic interstitial infusion of protein to primate brain: determination of drug distribution and clearance with single-photon emission computerized tomography imaging" *Journal of Neurosurgery* 87:586-594 (1997).

Lieberman et al. "Convection-enhanced distribution of large molecules in gray matter during interstitial drug infusion" *Journal of Neurosurgery* 82:1021-1029 (1995).

Lonser et al. "Successful and safe perfusion of the primate brainstem: in vivo magnetic resonance imaging of macromolecular distribution during infusion" *Journal of Neurosurgery* 97:905-913 (2002).

Mamot et al. "Extensive distribution of liposomes in rodent brains and brain tumors following convection-enhanced delivery" *Journal of Neuro-Oncology* 68:1-9 (2004).

Mardor et al. "Monitoring Response to Convection-enhanced Taxol Delivery in Brain Tumor Patients Using Diffusion-weighted Magnetic Resonance Imaging" *Cancer Research* 61:4971-4973 (2001).

Marshall et al. "Biocompatibility of Cardiovascular Gene Delivery Catheters with Adenovirus Vectors: An Important Determinant of the Efficiency of Cardiovascular Gene Transfer" *Molecular Therapy* 1(5):423-429 (2000).

Morrison et al. "High-flow microinfusion: tissue penetration and pharmacodynamics" *American Journal of Physiology—Regulatory, Integrative and Comparative Physiology* 266:R292-R305 (1994).

Morrison et al. "Focal delivery during direct infusion to brain: role of flow rate, catheter diameter, and tissue mechanics" *American Journal of Physiology—Regulatory, Integrative and Comparative Physiology* 277:R1218-R1229 (1999).

Naimark et al. "Adenovirus-Catheter Compatibility Increases Gene Expression After Delivery to Porcine Myocardium" *Human Gene Therapy* 14:161-166 (2003).

Pardridge, William M. "Drug Delivery to the Brain" *Journal of Cerebral Blood Flow and Metabolism* 17:713-731 (1997).

Pardridge, William M. "The Blood-Brain Barrier: Bottleneck in Brain Drug Development" *NeuroRx: The Journal of the American Society for Experimental NeuroTherapeutics* 2:3-14 (2005).

Patel et al. "Intraputamenal Infusion of Glial Cell Line-Derived Neurotrophic Factor in PD: A Two-Year Outcome Study" *Annals of Neurology* 57:298-302 (2005).

Qureshi et al. "Multicolumn Infusion of Gene Therapy Cells into Human Brain Tumors: Technical Report" *Neurosurgery* 46(3):663-669 (2000) (Abstract Only).

Richardson et al. "Interventional MRI-guided Putaminal Delivery of AAV2-GDNF for a Planned Clinical Trial in Parkinson's Disease" *Molecular Therapy* 19(6):1048-1057 (2011).

Rogawski, Michael A. "Convection-Enhanced Delivery in the Treatment of Epilepsy" *Neurotherapeutics: The Journal of the American Society for Experimental NeuroTherapeutics* 6:344-351 (2009).

Saito et al. "Convection-Enhanced Delivery of Tumor Necrosis Factor-Related Apoptosis-Inducing Ligand with Systemic Administration of Temozolomide Prolongs Survival in an Intracranial Glioblastoma Xenograft Model" *Cancer Research* 64:6858-6862 (2004).

Saito et al. "Distribution of Liposomes into Brain and Rat Brain Tumor Models by Convection-Enhanced Delivery Monitored with Magnetic Resonance Imaging" *Cancer Research* 64:2572-2579 (2004).

Tsui et al. "Stability of Adenoviral Vectors Following Catheter Delivery" *Molecular Therapy* 3(1):122-125 (2001).

Vogelbaum, Michael A. "Convection enhanced delivery for the treatment of malignant gliomas: symposium review" *Journal of Neuro-Oncology* 73:57-69 (2005).

Westphal et al. "Perspectives of cellular and molecular neurosurgery" *Journal of Neuro-Oncology* 70:255-269 (2004).

* cited by examiner

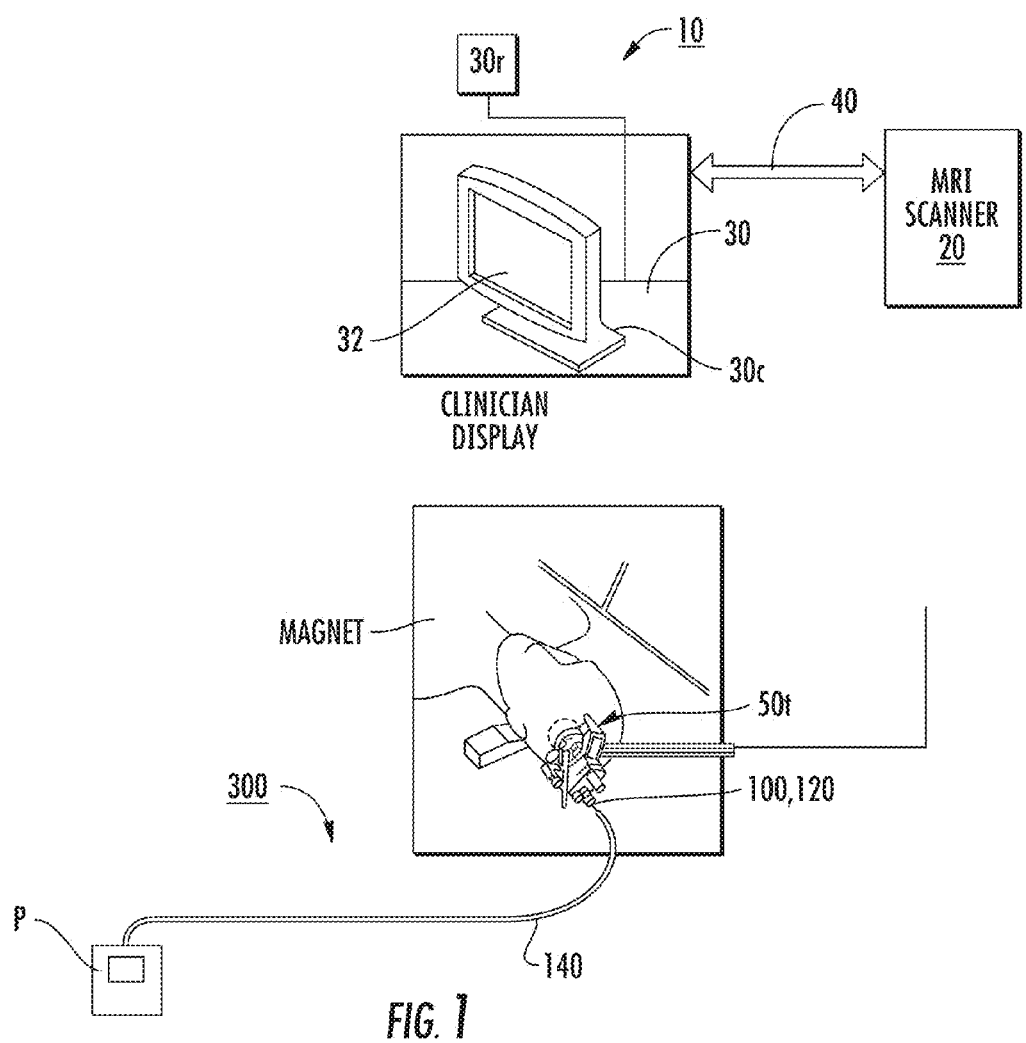

PROXIMAL FITTINGS

DISTAL TIPS

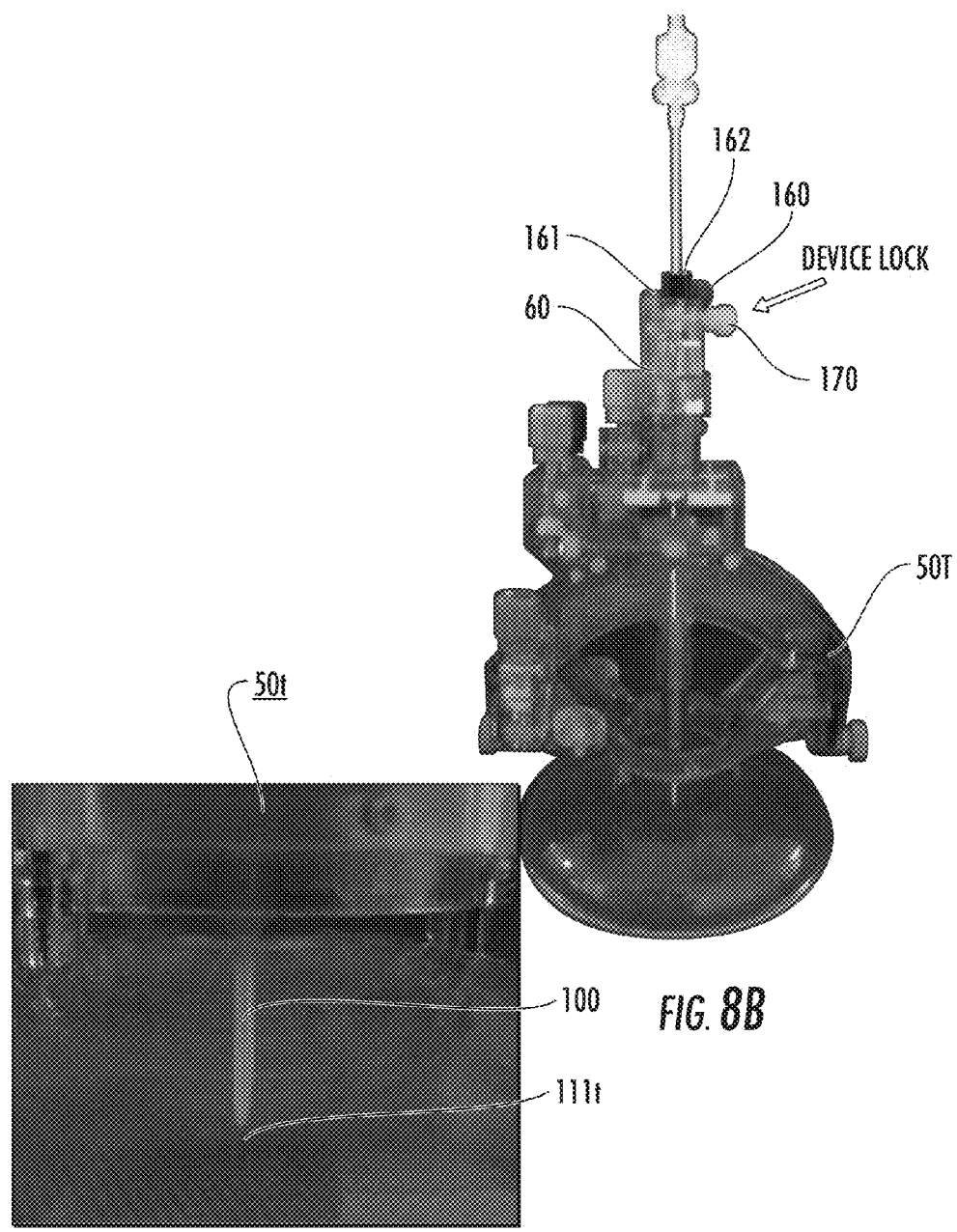

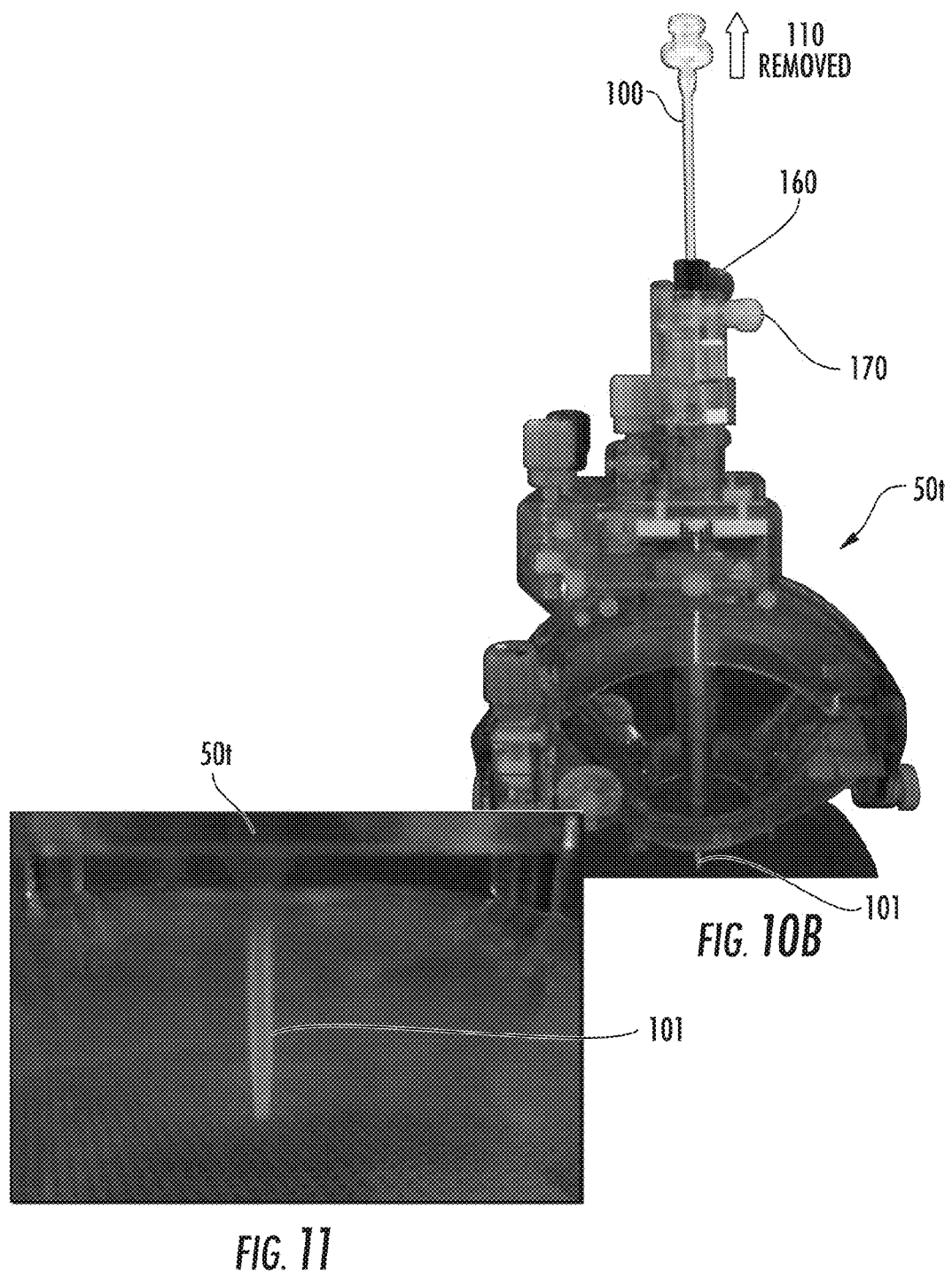

INTRABODY FLUID TRANSFER DEVICES, SYSTEMS AND METHODS

RELATED APPLICATIONS

This application claims the benefit of and priority to U.S. Provisional Application Ser. No. 61/877,451, filed Sep. 13, 2013, the contents of which are hereby incorporated by reference as if recited in full herein.

FIELD OF THE INVENTION

The present invention relates generally to medical devices and systems and, more particularly, to devices and systems for delivering and/or withdrawing substances in vivo, and may be particularly suitable for MRI-guided procedures.

BACKGROUND

Various therapeutic and diagnostic procedures require that a substance be delivered (e.g., infused) into a prescribed region of a patient, such as to an intrabody target using a delivery device. It may be important or critical that the substance be delivered with high accuracy to the target region in the patient and without undue trauma to the patient.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the invention are directed to a surgical device for transferring fluid to or from a subject. The device includes an elongate guide cannula having opposing proximal and distal ends with an open axially extending lumen. The proximal end includes a connector and an elongate needle having opposing proximal and distal ends. The needle has a connector that is configured to attach to the guide cannula connector. A portion of the needle resides in and/or is attached to or attachable to a length of flexible tubing. The elongate needle is configured to be slidably inserted into the guide cannula lumen so that the distal end of the needle extends out of the distal end of the distal end of the guide cannula a distance between The elongate needle can be formed of fused silica glass. The distal end of the needle can have a stepped configuration with a first segment having a first outer diameter that merges into a second end segment having a second smaller outer diameter, the second segment having a length that extends to a tip of the needle.

The distance that the needle extends out of the guide cannula is between about 2 mm to about 30 mm.

The needle connector can releasably attach to the elongate guide cannula connector, and wherein the flexible tubing is attached to a proximal end portion of the guide cannula connector and extends above the connector to encase a length of the needle therein.

The device can include an elongate stylet having opposing proximal and distal ends, the distal end having a sharp tip and the proximal end comprising a connector that releasably attaches to the elongate cannula connector. The stylet can have a body that is slidably receivable in the cannula lumen.

The needle can be a fused silica glass needle that has a length that extends above the needle-cannula connector. At least a major portion of the needle above the needle-cannula connector resides inside the flexible tubing.

The device can include a depth stop with an open lumen, the depth stop configured to reside about on an outer surface of the elongate guide cannula.

The elongate guide cannula can include a ceramic material.

The elongate guide cannula can have an outer polymeric coating and/or sleeve.

The distal end of the guide cannula can be tapered so that it has a smaller outer diameter at a tip relative to an outer diameter of the guide cannula rearward of the tapered distal end.

The elongate needle can be an infusate needle that has a stepped distal end configuration and is integrally attached to the flexible tubing as a subassembly. The device can also include a metal elongate stylet with a sharp tip on a distal end and a connector on a proximal end. The stylet and needle can be releasably interchangeably attachable to the guide cannula connector. The needle, stylet and guide cannula are all MRI compatible for use in an MRI guided procedure.

Other embodiments are directed to MRI compatible intrabody fluid transfer devices for transferring a substance to and/or from a patient. The devices include a rigid tubular guide cannula having an open lumen extending therethrough with a connector on a proximal end thereof and a needle with a connector and flexible tubing encasing a length of the needle above the connector. The needle is configured to be slidably insertable into the rigid guide cannula so that the needle connector attaches to the guide cannula connector and the distal end portion of the needle extends beyond the guide cannula.

The device can also include a metal stylet with a connector configured to releasably interchangeably attach to the tubular guide cannula connector in place of the needle with the needle connector.

The tubular guide cannula can be formed of or include a ceramic material.

The tubular guide cannula can have an outer polymeric coating and/or sleeve.

The distal end of the tubular guide cannula can be tapered so that it has a smaller outer diameter at a tip relative to an outer diameter of the guide cannula rearward of the tapered distal end.

The tubular guide cannula can include a ceramic material and a conformal outer polymeric sleeve.

The distal end portion of the needle that extends out of the tubular guide cannula can have at least first and second co-axially disposed segments having different outer diameters, with a smallest sized outer diameter of the first segment extending to a tip thereof.

The guide cannula can have an exterior surface on a distal end portion thereof that tapers down in size to a tip thereof to define a third coaxially disposed stepped segment that resides a distance rearward of the second segment and has a larger outer diameter than both the first and second co-axially disposed segments.

The needle can have a fused glass silica body with a single continuous lumen with at least a major portion of its length residing inside flexible tubing.

An outer surface of the guide cannula can have a size and geometry adapted for use with a stereotactic frame.

The needle can have an inner diameter of between about 100 μm to about 750 μm.

The first smallest outer diameter segment can have a longitudinal length of between about 1 mm to about 10 mm. The second segment can have a longitudinal length of between about 2 mm to about 20 mm. The distal tip of the guide cannula can reside a distance between 3 mm to about 30 mm from a distal tip of the needle.

Yet other embodiments are directed to methods of transferring a substance to and/or from a patient, the methods include: providing a guide cannula with a connector and an axially extending interior lumen; inserting a stylet with a sharp distal tip into the guide cannula lumen and attaching the stylet to the guide cannula so that the distal tip extends a distance outside the guide cannula distal end; placing the attached guide cannula and stylet into a trajectory guide of a stereotactic frame; then introducing the guide cannula and stylet into a subject so that the distal end of the guide cannula resides proximate a target site; then slidably withdrawing the stylet from the guide cannula and out of the subject, while leaving the guide cannula in position; then inserting a needle having an internal lumen into the guide cannula lumen and attaching a proximal end portion of the needle to the guide cannula while a distal end of the needle extends out of the guide cannula and resides at the target site; then transferring the substance to or from the target site through the needle lumen.

The needle can be an infusion needle. The transferring the substance to or from the target site can be carried out by infusing a substance.

Still other embodiments are directed to an MRI compatible infusion needle for transferring a substance to and/or from a patient. The needle includes an elongate fused silica needle comprising a body with a guide cannula connector that is adapted to connect to a guide cannula, the connector residing spaced apart from a distal tip of the needle. The needle body has a length that starts proximate and rearward of the guide cannula connector that is encased in flexible tubing. An exterior surface of the distal end of the needle has at least first and second co-axially disposed segments having different outer diameters.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 1 is a schematic illustration of an MRI-guided interventional system in which embodiments of the present invention may be utilized.

FIG. 8A is a side perspective view and FIG. 8B is a corresponding digital photograph of the stylet and cannula assembly as the assembly is inserted through a trajectory guide according to embodiments of the present invention.

FIG. 9 is an enlarged side view of the distal end of the assembly shown in FIG. 8A/8B according to some embodiments of the present invention.

FIG. 10A is a side perspective view and FIG. 10B is a corresponding digital photograph of the stylet removed from the cannula and the cannula remains in place in the trajectory guide according to embodiments of the present invention.

FIG. 11 is an enlarged digital image of a side view of the distal end of the assembly shown in FIGS. 10A/10B according to some embodiments of the present invention.

DETAILED DESCRIPTION

Figure 2A:
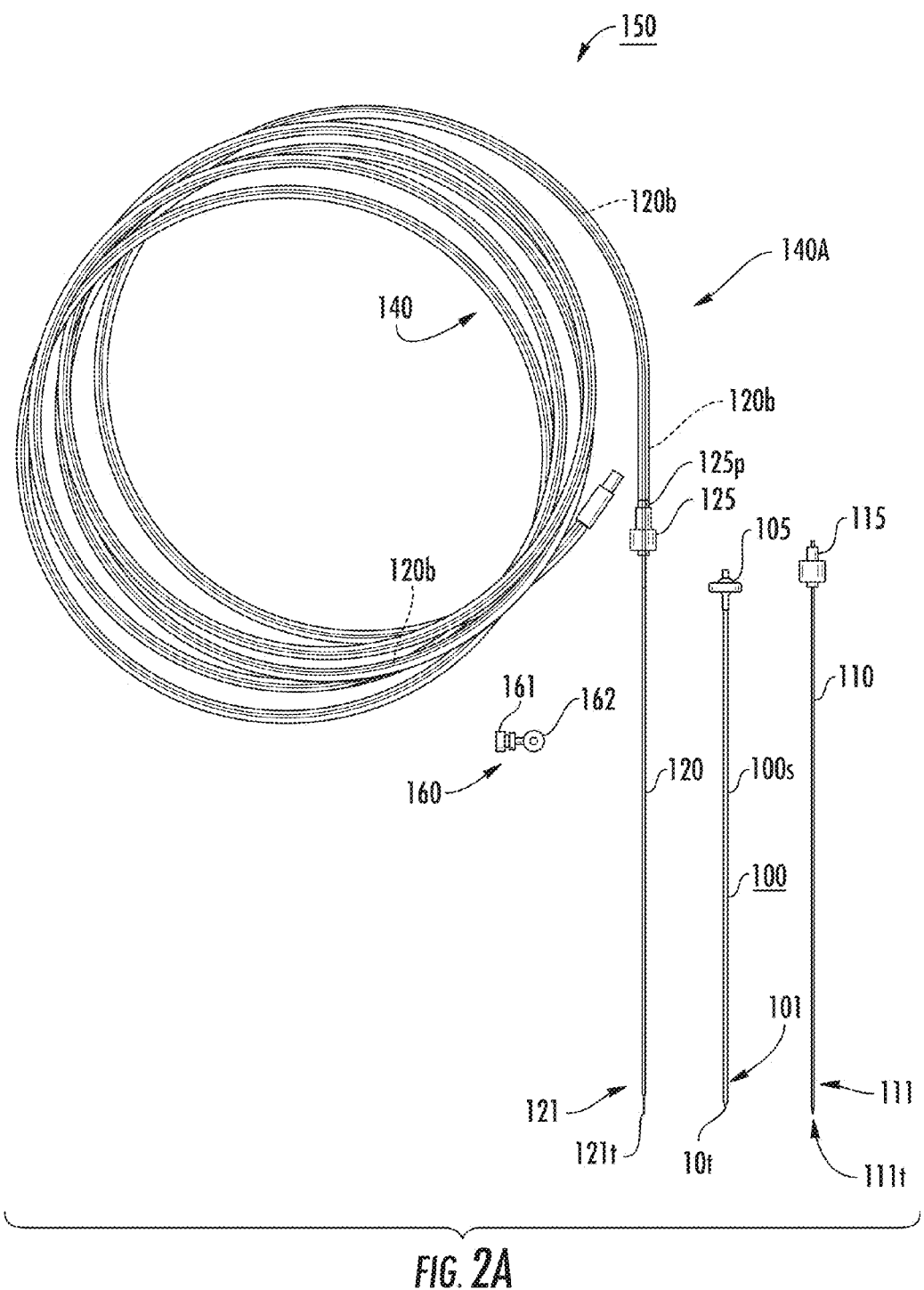
FIG. 2A is a top view of an exemplary infusion kit according to embodiments of the present invention.
Figure 2B:
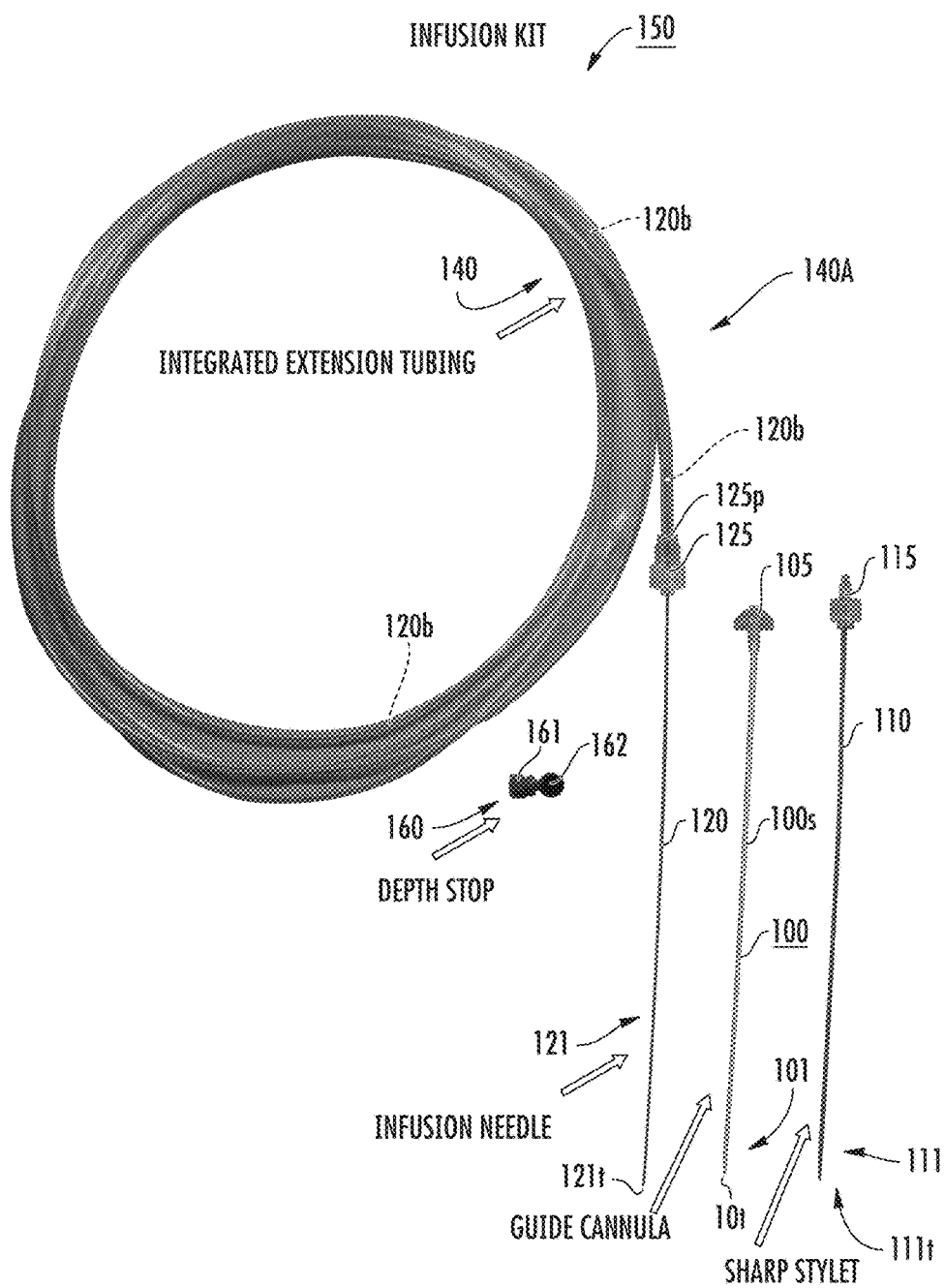
FIG. 2B is a digital photograph of the kit shown in FIG. 2A.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

The term "about," as used herein with respect to a value or number, means that the value or number can vary by +/−twenty percent (20%).

The term "monolithic" means that the component (e.g., needle) is formed of a single uniform material.

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5 T (Tesla), typically above 1.0 T, and more typically between about 1.5 T and 10 T.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near "real-time" imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., stylet) and the near RT MR image(s) are generated.

The term "sterile," as used herein, means that a device, kit, and/or packaging meets or exceeds medical/surgical cleanliness guidelines, and typically is free from live bacteria or other microorganisms.

Embodiments of the present invention can be utilized with various diagnostic or interventional devices and/or therapies to any desired internal region of an object using MRI and/or in an MRI scanner or MRI interventional suite. The object can be any object, and may be particularly suitable for animal and/or human subjects for e.g., animal studies and/or veterinarian or human treatments. Some embodiments deliver therapies to the spine. Some embodiments deliver therapies to treat or stimulate a desired region of the sympathetic nerve chain. Other uses, inside or outside the brain, nervous system or spinal cord, include stem cell placement, gene therapy or drug delivery for treating physiological conditions, chemotherapy, drugs including replicating therapy drugs. Some embodiments can be used to treat tumors.

The term "substance," as used herein, refers to a liquid for treating or facilitating diagnosis of a condition and can include bions, stem cells or other target cells to site-specific regions in the body, such as neurological, nerves or other target sites and the like. In some embodiments, stem cells and/or other rebuilding cells or products can be delivered into spine, brain or cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

The term "infusion" and derivatives thereof refers to the delivery of a substance (which can be a single substance or a mixture) at a relatively slow rate so that the substance can infuse about a target region. Thus, the term "infusate" refers to a substance so delivered.

Embodiments of the present invention will now be described in further detail below with reference to the figures. FIG. 1 illustrates an MRI-guided interventional system 10 with an MRI scanner 20, a clinician workstation 30 with at least one circuit 30c, at least one display 32, an MRI compatible trajectory guide 50t and a fluid transfer assembly 300 (FIGS. 14A/14B) comprising a guide cannula 100 and needle 120. In some embodiments, the fluid delivery assembly 300 can cooperate with an automated infusion pump P (FIG. 1) or, less preferably, a manual syringe or other pressurized delivery source.

The system 10 can be configured to render or generate near real time or real time visualizations of the target anatomical space using MRI image data and predefined data of at least one surgical tool (e.g., guide cannula 100 and/or trajectory guide 50t) to segment the image data and place the trajectory guide 50t and the cannula 100 in the rendered visualization in the correct orientation and position in 3D space (which is the MRI surgical space for MRI embodiments), anatomically registered to a patient. The trajectory guide 50t and the cannula 100 can include or cooperate with tracking, monitoring and/or other interventional components.

An exemplary trajectory guide 50t is illustrated in FIG. 1 in an exemplary (head) position on a patient. However, the trajectory guide can be used for any target location including, for example, the spine. The trajectory guide 50t can be mounted over or on an object, e.g., patient or subject, so that the upper receiving tube 60 (FIGS. 3, 15A, 15B) is oriented substantially perpendicular to the entry location (typically for spinal uses) or may be mounted to extend outward from the patient entry location at an angle as shown in FIG. 1.

The trajectory guide 50t typically provides X-Y adjustment and pitch and roll adjustment in order to accurately position the cannula 100 at a desired location within a patient. For additional discussion of examples of suitable trajectory guides, see U.S. Pat. No. 8,374,677, the contents of which are hereby incorporated by reference as if recited in full herein. However, it is noted that other trajectory guide configurations may be used and embodiments of the invention are not limited by the examples of the trajectory guides herein.

According to some embodiments, the systems are configured to provide a substantially automated or semi-automated and relatively easy-to-use MRI-guided system with defined workflow steps and interactive visualizations. In particular embodiments, the systems define and present workflow with discrete steps for finding target and entry point(s), guiding the alignment of the targeting cannula to a planned trajectory, monitoring the insertion of the guide cannula 100, and adjusting the (X-Y) position in cases where the placement needs to be corrected. During steps where specific MR scans are used, the circuit or computer module can display data for scan plane center and angulation to be entered at the console. The workstation/circuit can passively or actively communicate with the MR scanner. The system can also be configured to use functional patient data (e.g., fiber tracks, fMRI and the like) to help plan or refine a target surgical site and/or access path.

FIGS. 2A/2B illustrate a sterile assembly or set of components that may be provided individually or as a kit 150 of components for fluid delivery of an infusate or biopsy collection, for example. As shown, the assembly or kit 150 can include the guide cannula 100, a stylet 110 and a needle 120.

In some embodiments, the needle 120 can be an infusion needle that is pre-attached to a length of flexible (extension) tubing 140 to be provided as an integrated subassembly 140A. In other embodiments, the tubing 140 can be provided as a component separate from the infusion needle 120 for assembly prior to or during a procedure. If so, the ends of the tubing 140 and/or needle 120 may be capped or held in sterile sleeves to maintain sterility or cleanliness.

In some embodiments, a length of the needle 120 is encased in the flexible tubing 140. The length may be a short or long length. The flexible tubing 140 can be attached to a proximal end 125p of the guide cannula connector 125. The flexible tubing 140 can protect a long length of the needle where such a configuration is used.

In some embodiments, the needle 120 can be one continuous piece of fused silica glass that goes from the distal tip all the way to the very proximal end, typically between about 4 feet to about 10 feet long. Proximal to the connector 125 that locks the guide cannula 100 to the needle 120, the flexible tube 140 can be attached to reside over (encase) the needle body (e.g., of fused silica) 120b to protect the needle body as it may lay across a floor or a table as it travels to an infusion pump or manual syringe. Thus, the delivery substance A can be delivered through the needle so that it only touches the single piece of fused silica of the needle body 120b. However, the tubing 140 can be used to connect the needle 120 to the pump or other pressurized source and the delivery substance A can flow through the tubing 140 to the needle 120 for delivery. Further, other MRI compatible needle materials may be used.

According to some embodiments, the tubing 140 is PVC tubing. According to some embodiments, the tubing 140 is silicone tubing. The tubing 140 may have various lengths. For example, in some embodiments, the tubing may be between about four to about ten feet (4 ft-10 ft) in length, although other lengths are possible. At least a major portion (50% or greater) of a length of the needle body 120 can reside in the flexible tubing 140.

The kit 150 can be a single-use disposable kit of components. The kit 150 can be provided in other groups or sub-groups of components and does not require all components shown. The components can also be provided individually, typically in suitable sterile packaging.

The assembly or kit 150 can also include an optional depth stop 160 that can be slidably attached to reside proximate an upper to mid-portion of the outer diameter of the guide cannula 100. The depth stop 160 can include a small sleeve with an open lumen 162 that can receive the cannula 100. Optionally, the depth stop may include a laterally outwardly extending member 161 such as a thumb screw. The depth stop 160 configured to be slide over the outer diameter of the guide cannula 100 to snugly reside about the outer surface of the elongate guide cannula. The depth stop 160 can reside above and abut a lock 170 (FIGS. 3, 8A, 8B, 10A, 10B) on the trajectory guide 50t. The lock 170 and depth stop can lock the cannula 100 into a desired longitudinal position relative to the trajectory guide 50t. The cannula 100 can cooperate with and/or be secured to the trajectory guide 50t using other configurations including frictional engagement of surface features of the guide 50t and/or cannula 100, e.g., bumps, clamps, locking washers, O-rings and grooves and the like.

The cannula 100 can be securely held so that the tip 101t of the guide cannula resides at a specified intrabody location, typically a short distance "$D_1$" (FIG. 3) of between about 1 mm to about 50 mm above an actual infusate target site S. Stated differently, in an intrabody delivery position, the distal end of the cannula 101 resides above the tip 121t at the distal end of the infusate needle 121.

The needle 120 can be slidably and releasably attached to the guide cannula 100 to form a subassembly 300 (FIGS. 12A, 12B, 14A, 14B). Typically, the needle is attached to the cannula 100 after the cannula is in position in the body and the stylet has been removed (FIGS. 10A, 10B, 12A, 12B, 13). The needle 110 can have a connector 125 on its proximal end. Where the needle 120 is an infusion needle, the needle body 120b can extend a distance above the connector 125 into the flexible extension tubing 140 a defined length as discussed above.

The infusion needle 120 can have a body 120b of fused silica (glass) that can be configured to define a single open lumen that extends from the end of the tip 120t to the proximal end of the needle body 120b so that the lumen is in fluid communication with the flexible tubing 140. Optionally, the needle 120 can have an outer polymeric coating or sleeve such as a shrink wrap material to provide protection from breakage or to contain fragments if such should break.

The guide cannula 100 can have a rigid body. The guide cannula 100 may comprise alumina/ceramic that can be MRI visible. The guide cannula 100 can have an outer surface 100s having a lubricious coating and/or sleeve 100s. The coating and/or sleeve 100s can be a substantially transparent polymeric material. Where a sleeve is used, the sleeve 100s can be a thin flexible polymeric sleeve that can be conformably attached to the underlying cannula body 100b. The coating and/or sleeve can be configured with sufficient strength to be able to retain components of the guide cannula should the cannula fracture. The sleeve can be an elastomeric shrink wrap or tube that can be heat-shrink applied to the underlying body.

In some embodiments, the stylet 110 is optional. For example, the distal end 101 of the guide cannula 100 may be sufficiently sharp to be able to penetrate tissue without undue trauma for certain procedures without requiring the stylet 110. Where used, the stylet 110 can be slidably attached to the guide cannula 100 using mating connectors 105, 115 on respective proximal ends of the devices. The stylet 110 can be metallic and provide structural support to the cannula during intrabody insertion. The stylet 110 can comprise a non-ferromagnetic metallic body with a sharp tip 110t that can pierce tissue or other target anatomy without undue trauma (e.g., in a minimally invasive manner). The stylet 110 can comprise titanium or a sufficient grade of stainless steel. The guide cannula 100 slidably receives the stylet 110 and allows the distal end 111 and/or tip 111t of the stylet to extend a short distance beyond the tip 101t of the guide cannula.

Advantageously, in contrast to single-piece infusion cannulas that do not have a separate needle, the multiple-piece construction allows for a less traumatic and/or stronger configuration during initial insertion of the cannula 100 in the body.

Figure 6A:
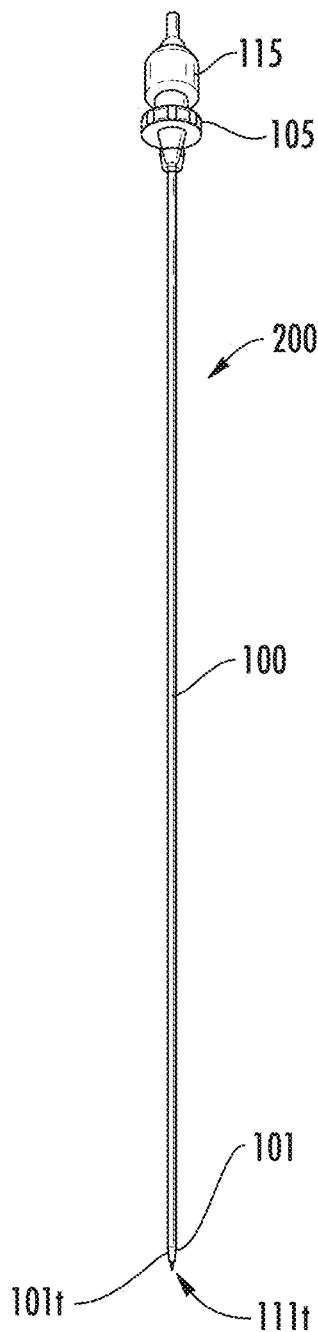
FIG. 6A is a side view and FIG. 6B is a corresponding digital photograph of a stylet and cannula assembly according to embodiments of the present invention.
Figure 6B:
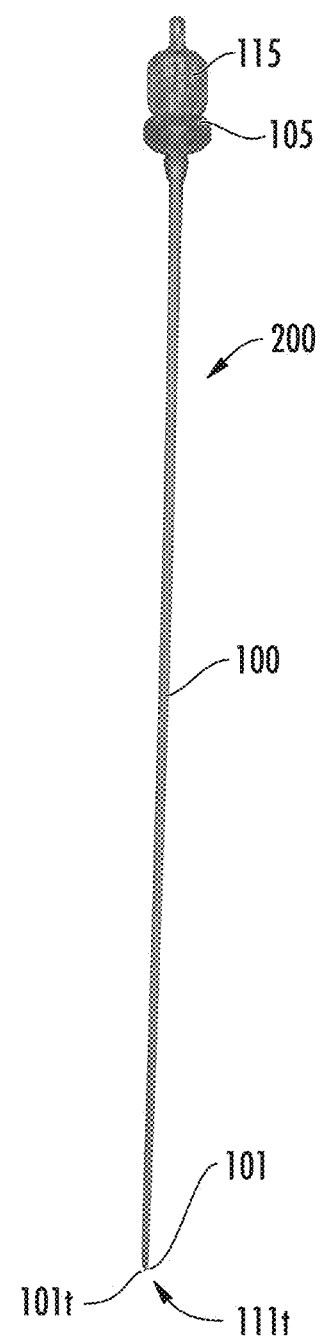
Figure 7A:
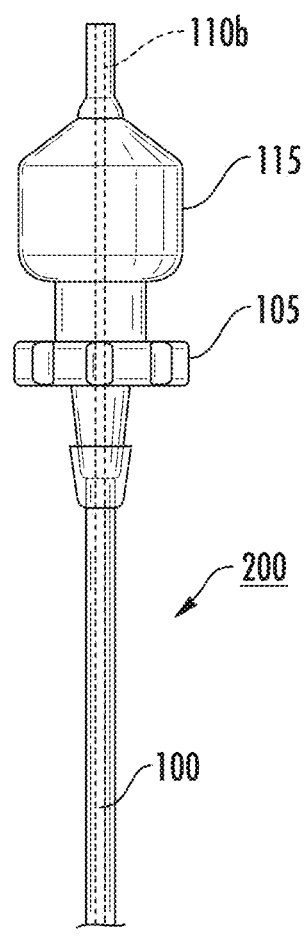
FIGS. 7A and 7B are enlarged side views of the proximal and distal end portions, respectively, of the assembly shown in FIG. 6A/6B.
Figure 7B:
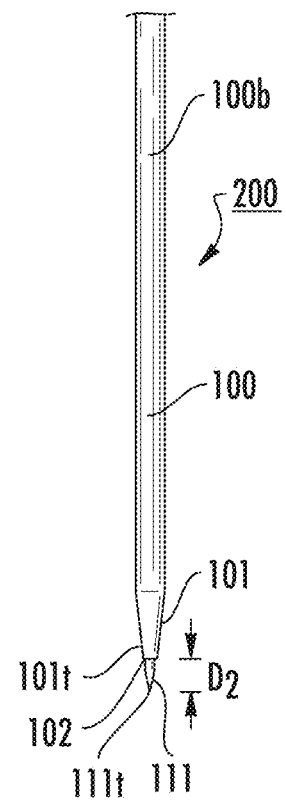

Although shown as separate components in FIGS. 2A/2B, the guide cannula 100 can be provided in the kit 150 as a subassembly 200 (FIGS. 6A/6B), where the guide cannula 100 and stylet 110 are releasably pre-attached (where the stylet is used).

The assembly 300 (FIGS. 3, 12A, 12B and 13) of the cannula 100 with the infusate needle 120 can be configured to flowably introduce and/or inject a desired therapy substance (e.g., antigen, gene therapy, chemotherapy or stem-cell or other therapy type).

Figure 5A:
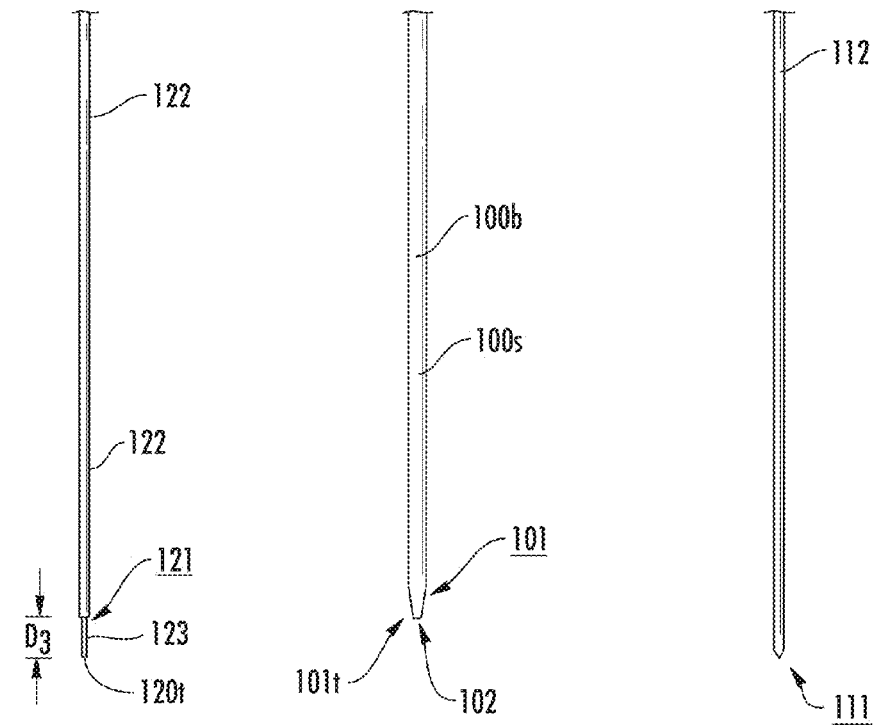
FIG. 5A is an enlarged side view and FIG. 5B is a corresponding digital photograph of distal end portions of the devices shown in FIG. 2A/2B according to some embodiments of the present invention.
Figure 5B:
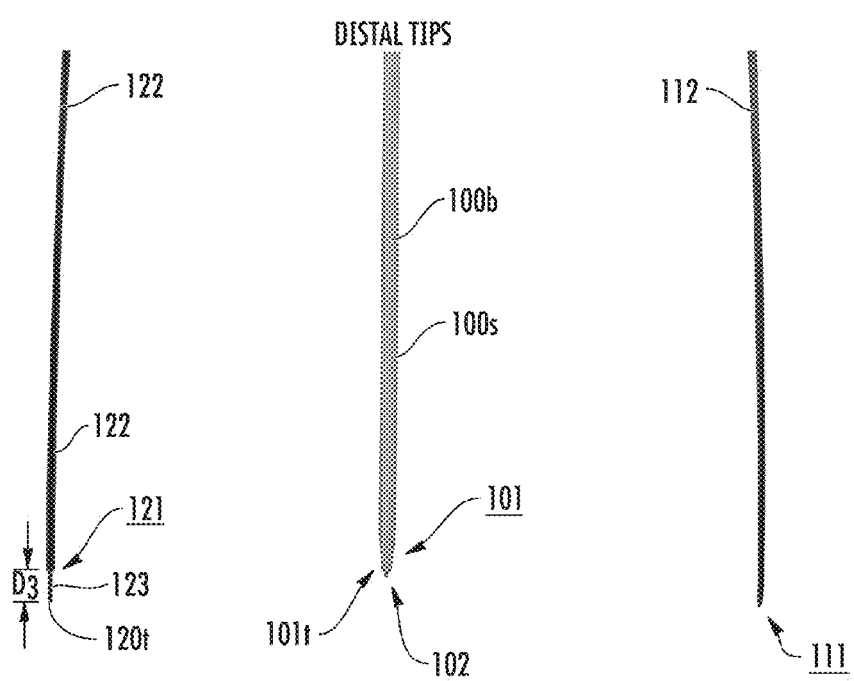

FIGS. 4A, 4B, 5A and 5B illustrate examples of the cannula 100, stylet 110 and infusion needle 120. Both the stylet 110 and infusion needle 120 can releasably interchangeably attach to the cannula 100 using respective connectors 105, 115, 125. The connectors can be threadably engage, have a bayonet fitting, or tongue and groove fittings or other releasable attachment configurations. As shown in FIGS. 5A/5B, the cannula 100 includes a cannula body 100b defining at least one longitudinally extending lumen 102. The cannula 100 typically is formed of an MRI-compatible (non-ferromagnetic) material such as ceramic as discussed above and can have a distal end 101 that tapers to a smaller outer diameter size relative to the outer diameter size of the cannula body 100b over most if not all of its length. The entire body 100b or markers on the body can be MRI visible for image segmentation and recognition. For additional discussion of features of exemplary cannulas that can be used with embodiments of the present invention, see U.S. Patent Application Publication No. US 2013/0030408, the contents of which are hereby incorporated by reference as if recited in full herein.

In some embodiments, the lumen 102 slidably receives the stylet 110 (FIGS. 6A, 6B, 7A, 7B) to form the stylet subassembly 200 with the distal end 111 and/or tip 111t of the stylet extending a distance $D_2$ beyond the cannula tip 101t. The distance $D_2$ can be less than $D_1$, and is typically between about 0.1 mm to about 5 mm.

Also shown in FIGS. 5A, 5B, 14A and 14B, the infusate needle 120 has a stepped distal end 121 where the outer diameter decreases in size toward the tip 121t. The body 120b can have a substantially constant (on average) outer diameter segment 122 that steps down into the smaller outer diameter (OD) segment 123 at the distal end 121 of the infusate needle. The smaller OD segment can 123 have a length $D_3$ that is between about 1 mm to about 50 mm, typically between 1 mm and 10 mm, and in some embodiments between about 2 mm to about 4 mm, such as about 3 mm. The second segment 122 can be longer than the first segment 123 and can be between about 2 mm and 20 mm. The distal end of the needle 121 may include more than two co-axially aligned (concentric) stepped segments.

Figure 3:
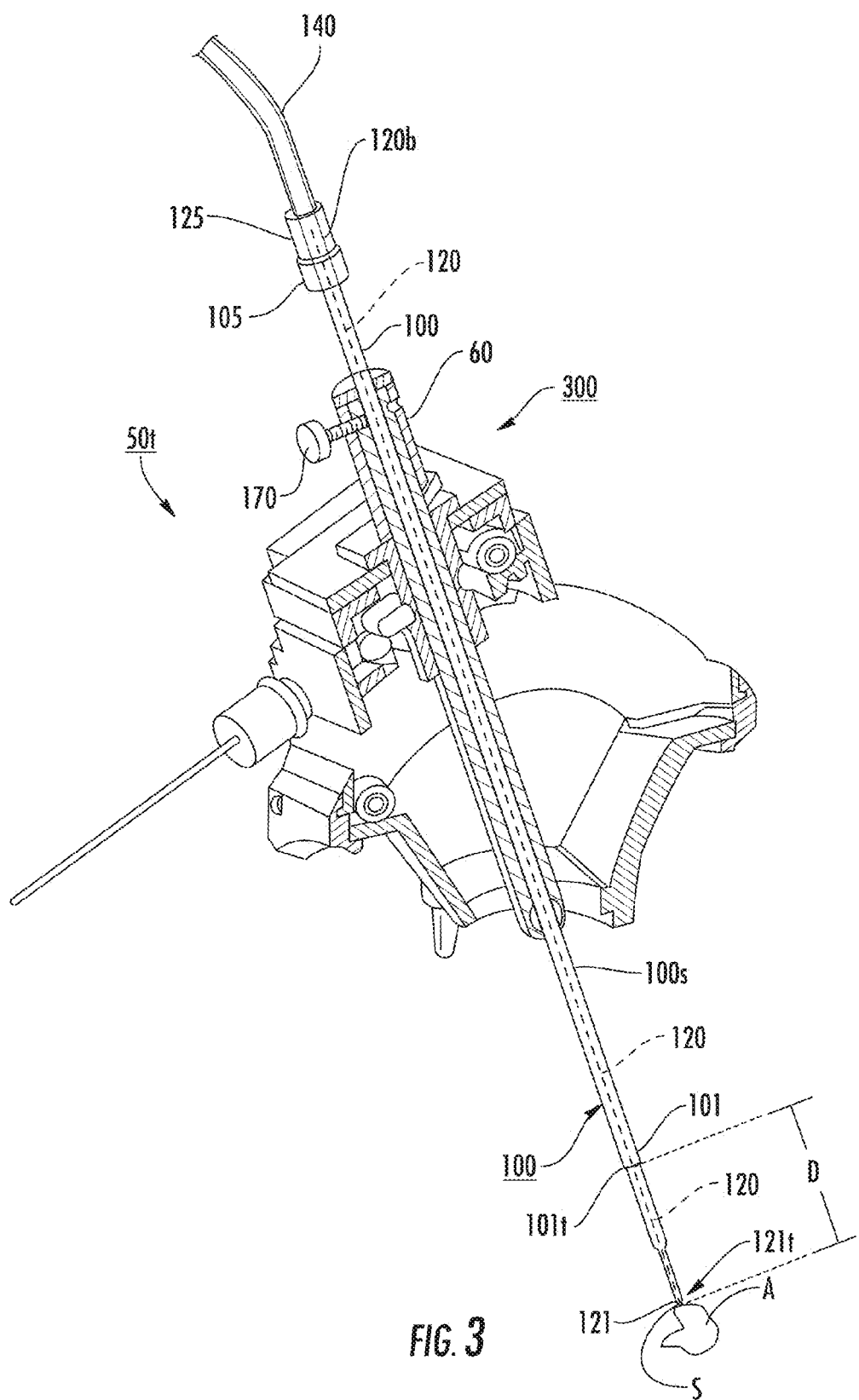
FIG. 3 is a sectional view of the trajectory guide of the MRI-guided system of FIG. 1 with an exemplary two-piece assembly (needle and surgical guide cannula) for transferring a substance (e.g., an infusate, etc.) to an intrabody target region of a patient.
Figure 4A:
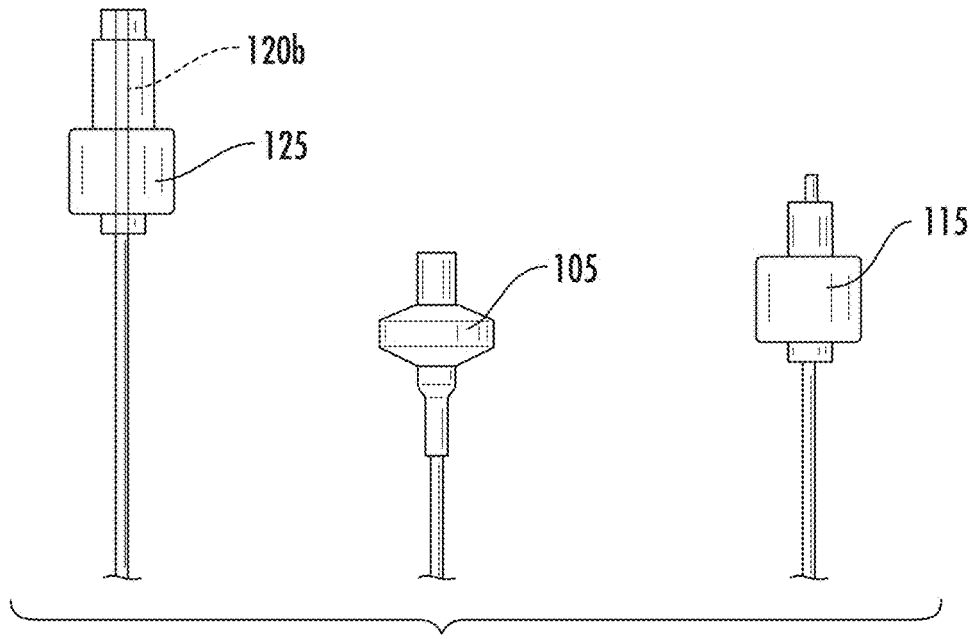
FIG. 4A is an enlarged side view and FIG. 4B is a corresponding digital photograph of proximal end portions of the devices shown in FIGS. 2A/2B according to some embodiments of the present invention.
Figure 4B:
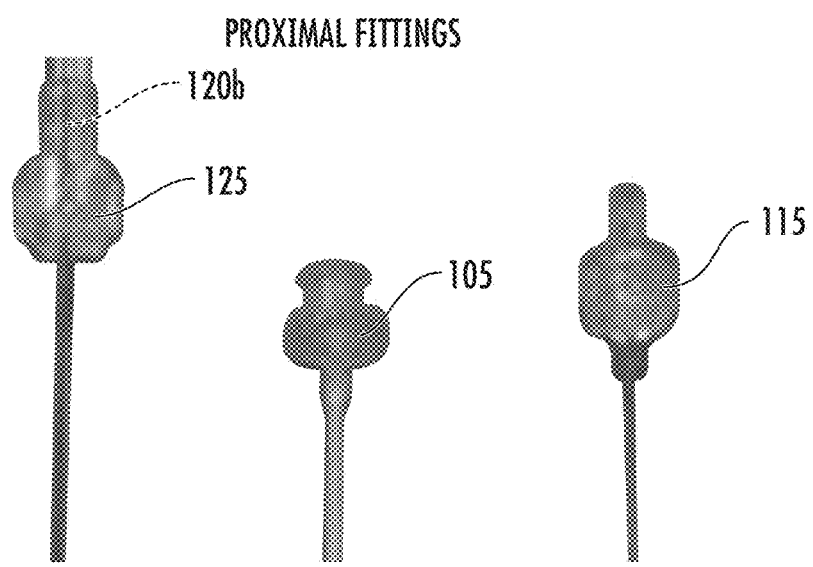
Figures 12B, 13:
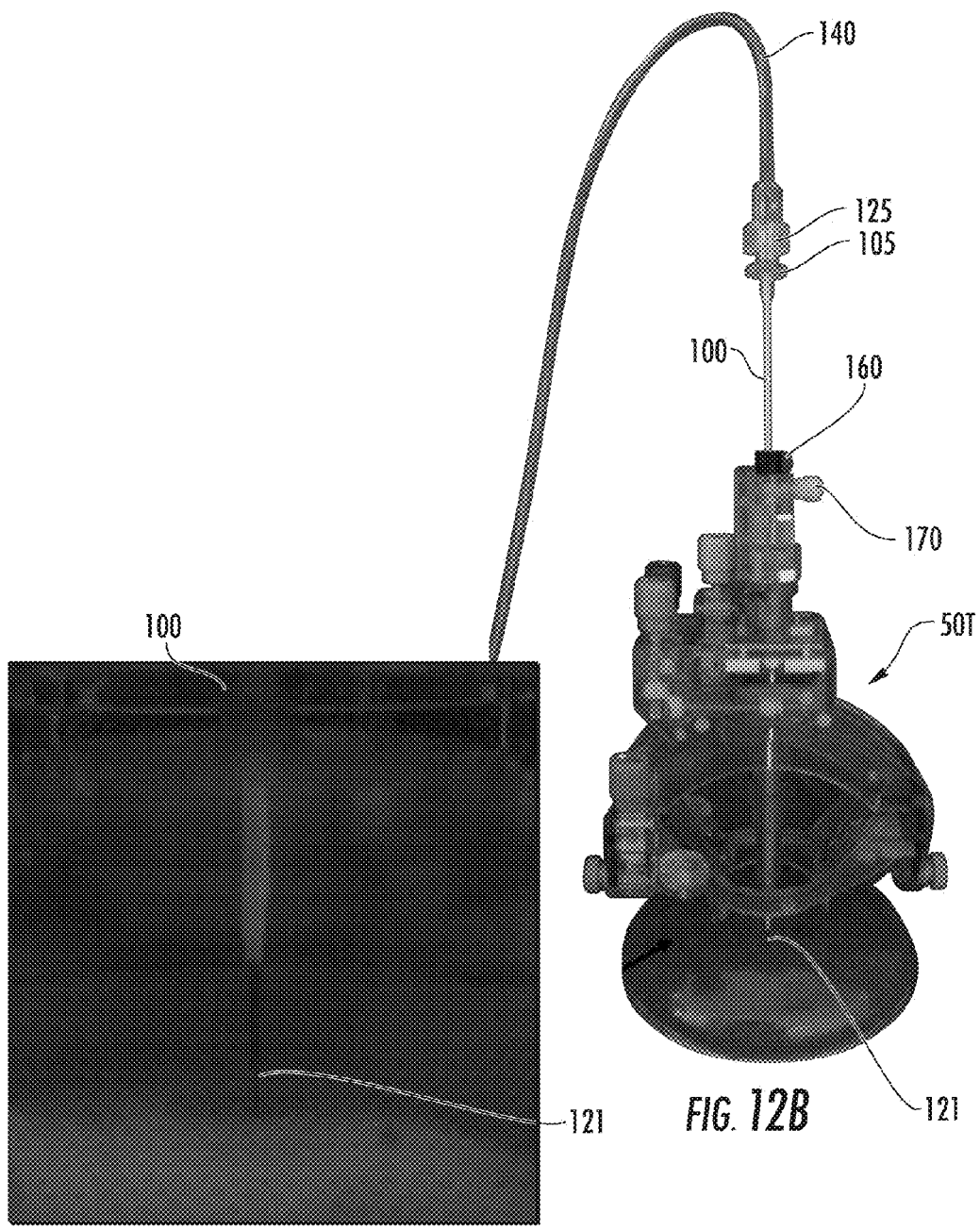
FIG. 13 is a digital photograph of an enlarged side view of the distal end of the assembly shown in FIG. 12A/12B according to some embodiments of the present invention.
Figure 14A:
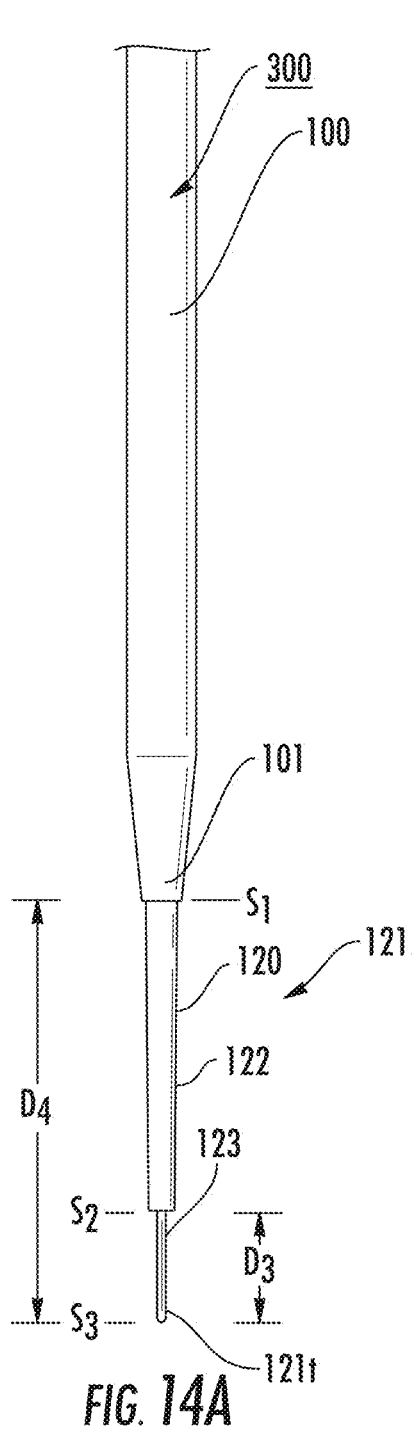
FIG. 14A is an enlarged view and FIG. 14B is a corresponding digital photograph of the distal end portion of the guide cannula and needle assembly illustrating an exemplary relative position of the distal end of the needle with respect to the distal end of the guide cannula according to embodiments of the present invention.
Figure 14B:
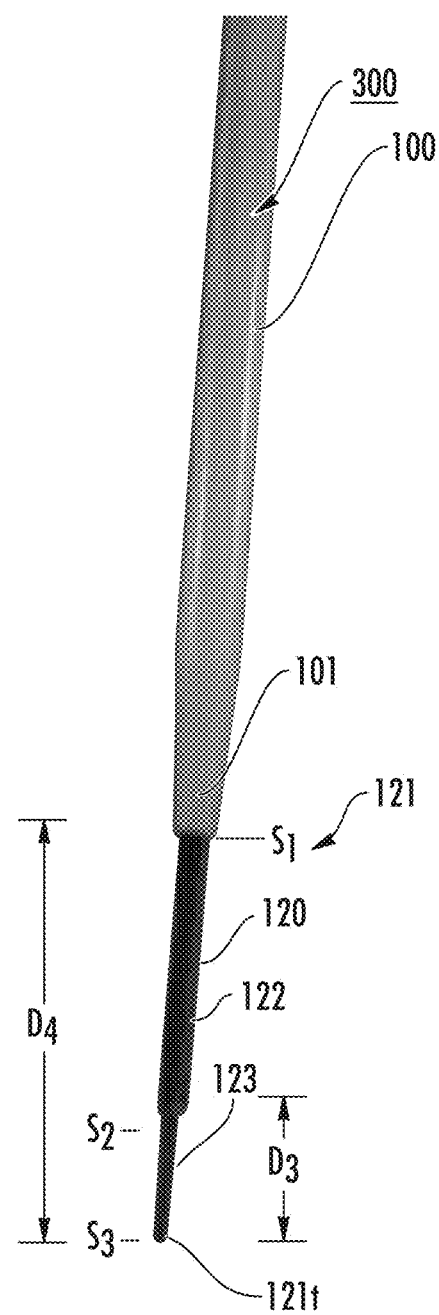

In position for delivery of the infusate A in the body, the tip 121t of the infusate needle 120 can extend a distance $D_4$ beyond the cannula tip 101t so that a portion of the larger OD segment 122 as well as the smaller OD segment 123 reside outside of the cannula tip 101t as shown in FIGS. 3, 13 and 14A/14B. The length $D_4$ of the distal end of the infusion needle outside the cannula 100 during delivery can be between about 3 mm to 30 mm. This configuration may inhibit reflux.

According to some embodiments, the inner diameter of the infusate needle 120 is in the range of from about 10 μm to 1 mm and, in some particular embodiments, is be between about 100 μm to about 750 μm, such as about 200 μm. According to some embodiments, the outer diameter is in the range of from about 75 μm to 1.08 mm and, in some embodiments is about 360 μm.

According to some embodiments, the cannula 100 has an outer surface comprising a polymeric support sleeve 100s which as a thickness in the range of from about 40 μm to about 60 μm.

As seen in FIGS. 14A/14B, the needle 120 can have a stepped end that cooperates with the tapered end of the cannula to form three co-axially disposed step segments (the outer surface of the distal end of the cannula 101, the first segment of the distal end of the needle 122 and the second segment of the distal end of the needle 123, respectively) having different outer diameters and being longitudinally separated with steps on end faces S1, S2, S3. The steps S1, S2, S3 can serve to reduce or prevent reflux of the delivered substance.

The infusate needle 120 connector 125 can be configured as a luer lock and the needle/tubing can be operatively coupled to an infusion pump P which supplies a mass flow of the desired substance or material to be delivered into the patient.

Referring again to FIGS. 4A, 4B, 5A and 5B, the stylet 110 can have a segment 112 that resides above the distal end thereof 111 with an outer diameter that is the same or slightly larger (on average) than the outer diameter of the needle segment 122 and can be configured to be slidably received in the guide cannula 100 to snugly reside in the lumen 102 of the guide cannula 100 for structural buttressing.

Figure 8A:
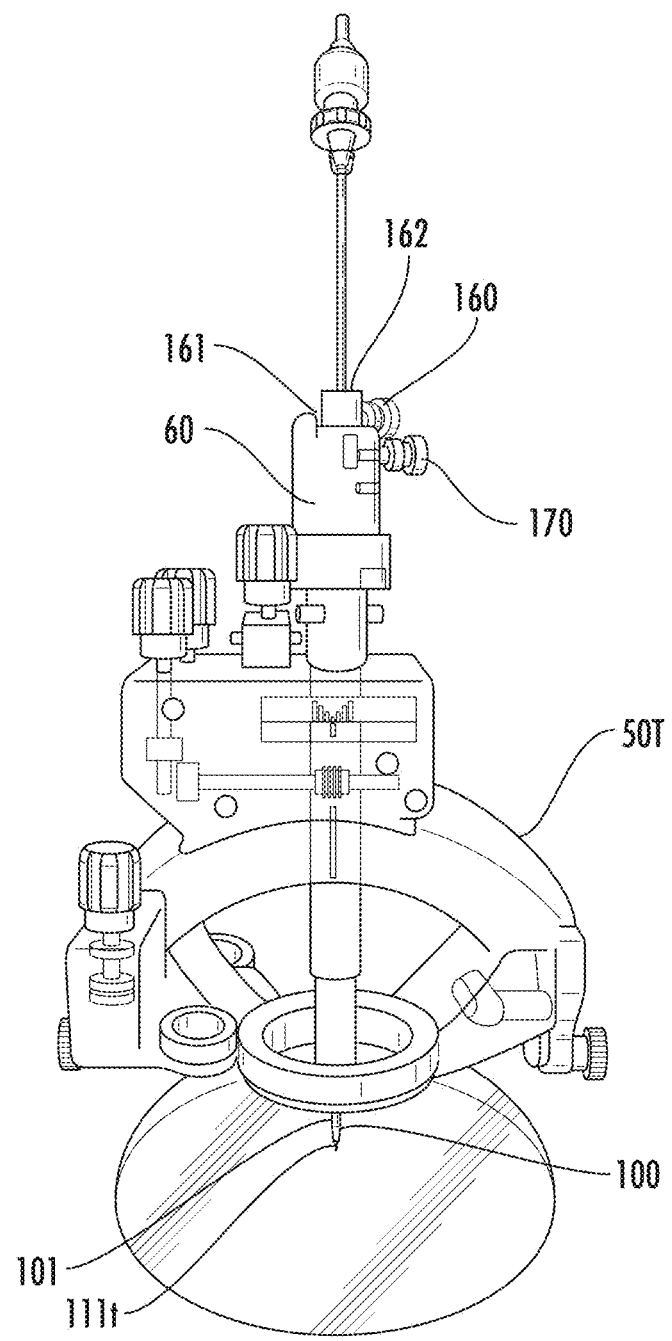

An exemplary sequence shown in FIGS. 8A/8B-13. As shown in FIGS. 8A/8B and 9, the stylet 110 is inserted into the cannula 100 to form the assembly 200. Typically, the assembly 200 is formed prior to insertion of the components into the trajectory guide, e.g., the assembly 200 is slidably inserted as a unit. However, the cannula 100 can be attached to the trajectory guide 50t first, then the stylet 110 can be inserted.

The trajectory guide 50t is held by a frame, e.g., a stereotactic frame, that can be secured to the patient or that can be secured to a holder residing over the patient. See, e.g., U.S. Pat. Nos. 8,315,689, 8,175,677 and 8,374,677 and US Patent Application Publication No. 2010/0198052 (Ser. No. 12/694,865) for descriptions of patient planning and entry protocols and frames and trajectory guides, the contents of which are hereby incorporated by reference as if recited in full herein.

The depth stop 160, where used, can be placed on the cannula 100 before the stylet 110 is inserted into the cannula 100 or after, but before the assembly 200 is inserted into the trajectory guide 50t. Optionally, the depth stop 160 can be pre-attached to the guide cannula 100 and provided as a subassembly in the kit 150.

Thus, as shown in FIGS. 8A/8B and 9, the stylet/cannula assembly 200 can be inserted into the receiving channel 60 of the trajectory guide 50t. The cannula 100 can be locked to the trajectory guide 50t using the lock 170 that can be laterally extended to rest against the outer surface of the cannula or against a cooperating feature on the cannula. The depth stop 160 can be adjusted to reside on top of the device lock 170 when the distal end of the cannula 101 is at a desired intrabody location.

Figure 10A:
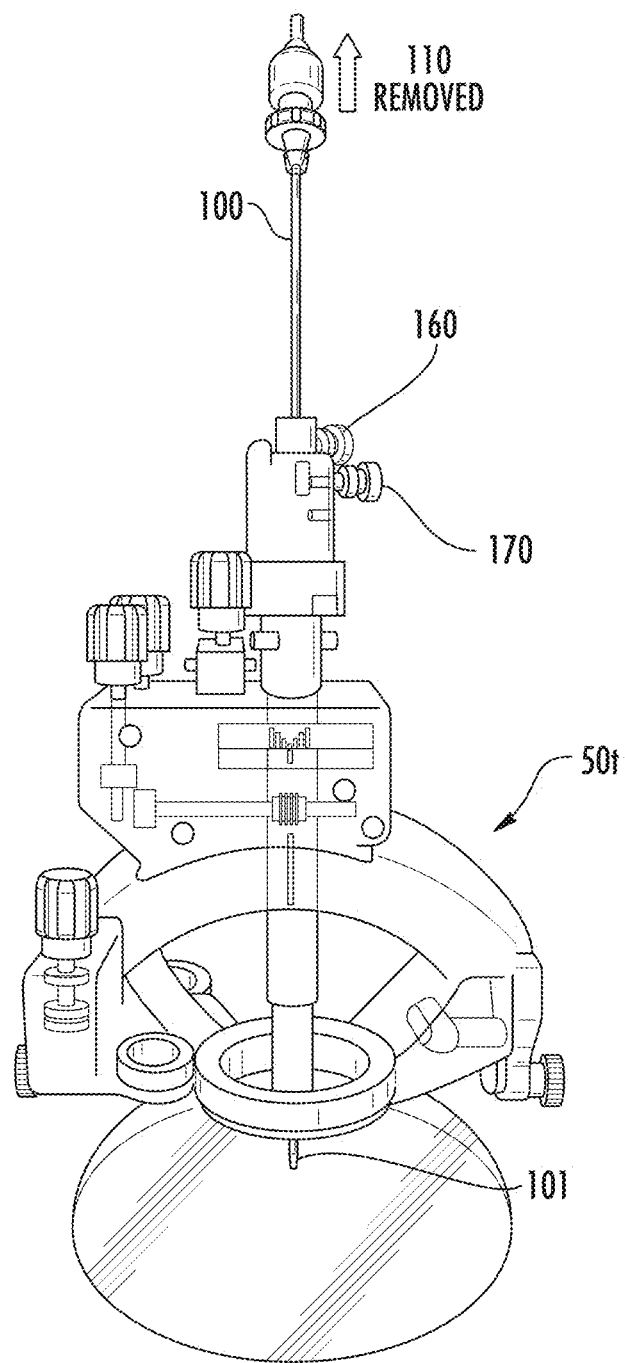

FIGS. 10A, 10B and 11 show that the stylet 110 can be removed from the guide cannula 100 while the guide cannula 100 remains locked in the trajectory guide 50t so that the distal end 101 of the guide cannula is proximate a desired target infusate delivery site (and/or a biopsy collection site).

Figure 12A:
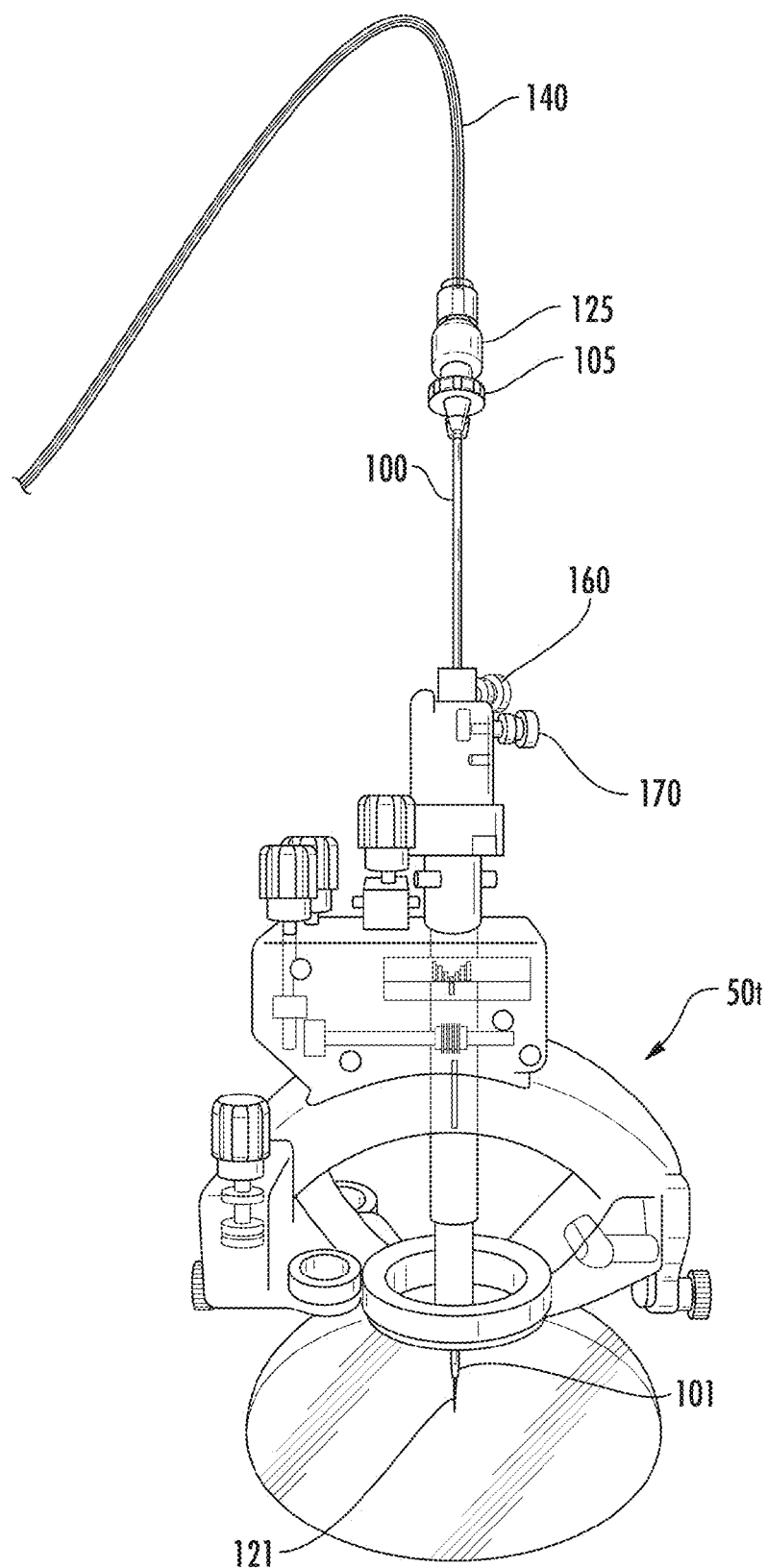
FIG. 12A is a side perspective view and FIG. 12B is a corresponding digital photograph of the needle inside the cannula as a needle and cannula assembly with the needle passing through the guide cannula held by the trajectory guide according to embodiments of the present invention.

FIGS. 12A, 12B and 13 illustrate that once the stylet 110 is removed from the guide cannula 100, the needle 120, typically an infusate needle, is slidably inserted into the guide cannula 10 and the connectors 125, 105 connected so that the distal end extends out of the distal tip of the guide cannula to reside at a target intrabody site A. FIGS. 14A/14B illustrate an exemplary configuration of the distal end of the needle 121 during active dispensing/infusate.

Figure 15A:
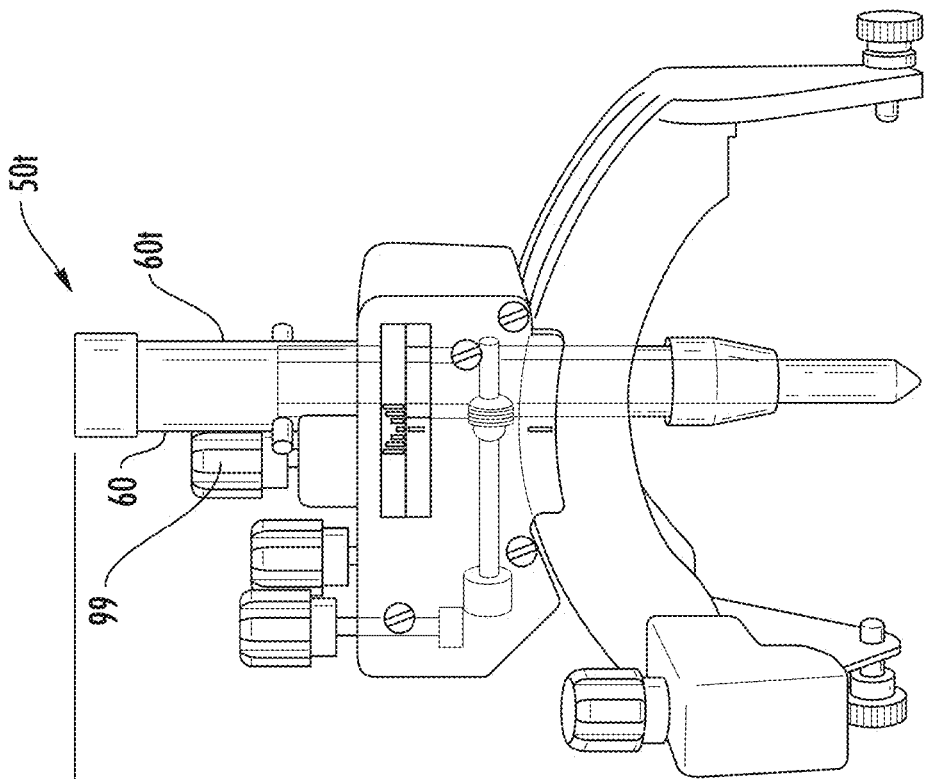
FIG. 15A is a side view of a trajectory guide with a short upper receiving member according to embodiments of the present invention.
Figure 15B:
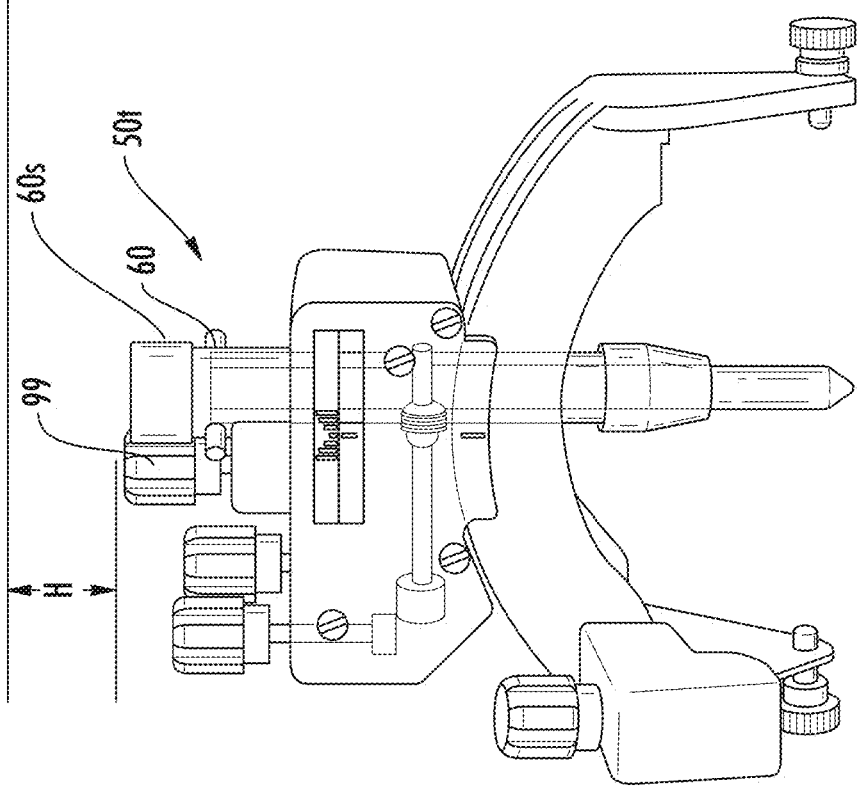
FIG. 15B is a side view of a trajectory guide with a longer upper receiving member according to embodiments of the present invention.

FIGS. 15A and 15B illustrate that the trajectory guide 50t can have different height H receiving channels 60, shown as short and tall channels 60s, 60t. The short channel 60s can be at about the same height as the tallest adjacent top-mounted actuator 99, and is typically about 2 cm shorter than the tall channel 60t and may be particularly suitable for vertical orientation inside a magnet bore to thereby avoid interference with the bore chamber.

The substance A (FIGS. 2A/2B) delivered to the target site or region S through the cannula guide 100 and cooperating needle 120 may be any suitable and desired substance for drug discovery, animal or human clinical trials and/or approved medical procedures. According to some embodiments, the substance A is a liquid or slurry. In the case of a tumor, the substance may be a chemotherapeutic (cytotoxic) fluid. In some embodiments, the substance can include certain types of advantageous cells that act as vaccines or other medicaments (for example, antigen presenting cells such as dendritic cells). The dendritic cells may be pulsed with one or more antigens and/or with RNA encoding one or more antigen. Exemplary antigens are tumor-specific or pathogen-specific antigens. Examples of tumor-specific antigens include, but are not limited to, antigens from tumors such as renal cell tumors, melanoma, leukemia, myeloma, breast cancer, prostate cancer, ovarian cancer, lung cancer and bladder cancer. Examples of pathogen-specific antigens include, but are not limited to, antigens specific for HIV or HCV. In some embodiments, the substance A may comprise radioactive material such as radioactive seeds. Substances A delivered to a target area in accordance with embodiments of the present invention may include, but are not limited to, the following drugs (including any combinations thereof) listed in Table 1:

TABLE 1

| DRUG (generic name) | DISORDER(S) |
| --- | --- |
| Caprylidene | Alzheimer's disease |
| Donepezil | Alzheimer's disease |
| Galantamine | Alzheimer's disease |
| Memantine | Alzheimer's disease |
| Tacrine | Alzheimer's disease |
| vitamin E | Alzheimer's disease |
| ergoloid mesylates | Alzheimer's disease |
| Riluzole | Amyotrophic lateral sclerosis |
| Metoprolol | Benign essential tremors |
| Primidone | Benign essential tremors |
| Propanolol | Benign essential tremors |
| Gabapentin | Benign essential tremors & Epilepsy |
| Nadolol | Benign essential tremors & Parkinson's disease |
| Zonisamide | Benign essential tremors & Parkinson's disease |
| Carmustine | Brain tumor |
| Lomustine | Brain tumor |

TABLE 1-continued

| DRUG (generic name) | DISORDER(S) |
| --- | --- |
| Methotrexate | Brain tumor |
| Cisplatin | Brain tumor & Neuroblastoma |
| Ioversol | Cerebral arteriography |
| Mannitol | Cerebral Edema |
| Dexamethasone | Cerebral Edema & Neurosarcoidosis |
| Baclofen | Cerebral spasticity |
| Ticlopidine | Cerebral thrombosis/embolism |
| Isoxsuprine | Cerebrovascular insufficiency |
| Cefotaxime | CNS infection & Meningitis |
| Acyclovir | Encephalitis |
| Foscarnet | Encephalitis |
| Ganciclovir | Encephalitis |
| interferon alpha-2a | Encephalitis |
| Carbamazepine | Epilepsy |
| Clonazepam | Epilepsy |
| Diazepam | Epilepsy |
| divalproex sodium | Epilepsy |
| Ethosuximide | Epilepsy |
| Ethotoin | Epilepsy |
| Felbamate | Epilepsy |
| Fosphenytoin | Epilepsy |
| Levetiracetam | Epilepsy |
| Mephobarbital | Epilepsy |
| Paramethadione | Epilepsy |
| Phenytoin | Epilepsy |
| Trimethadione | Epilepsy |
| Pregabalin | Epilepsy & Neuralgia |
| immune globulin intravenous | Guillain-Barre Syndrome |
| interferon beta-1b | Guillain-Barre Syndrome & Multiple sclerosis |
| Azathioprine | Guillain-Barre Syndrome & Multiple sclerosis & Neurosarcoidosis |
| Risperidone | Head injury |
| Tetrabenazine | Huntington's disease |
| Acetazolamide | Hydrocephalus & Epilepsy |
| Alteplase | Ischemic stroke |
| Clopidogrel | Ischemic stroke |
| Nimodipine | Ischemic stroke & Subarachnoid hemorrhage |
| Aspirin | Ischemic stroke & Thromboembolic stroke |
| Amikacin | Encaphalitis |
| Ampicillin | Encaphalitis |
| ampicillin/sulbactam | Encaphalitis |
| Ceftazidime | Encaphalitis |
| Ceftizoxime | Encaphalitis |
| Cefuroxime | Encaphalitis |
| Chloramphenicol | Encaphalitis |
| cilastatin/imipenem | Encaphalitis |
| Gentamicin | Encaphalitis |
| Meropenem | Encaphalitis |
| Metronidazole | Encaphalitis |
| Nafcillin | Encaphalitis |
| Oxacillin | Encaphalitis |
| Piperacillin | Encaphalitis |
| Rifampin | Encaphalitis |
| sulfamethoxazole/trimethoprim | Encaphalitis |
| Tobramycin | Encaphalitis |
| Triamcinolone | Encaphalitis |
| Vancomycin | Encaphalitis |
| Ceftriaxone | Encaphalitis & Neurosyphilis |
| Penicillin | Encaphalitis & Neurosyphilis |
| Corticotrophin | Multiple sclerosis |
| Dalfampridine | Multiple sclerosis |
| Glatiramer | Multiple sclerosis |
| Mitoxantrone | Multiple sclerosis |
| Natalizumab | Multiple sclerosis |
| Modafinil | Multiple sclerosis |
| Cyclophosphamide | Multiple sclerosis & Brain tumor & Neuroblastoma |
| interferon beta-1a | Multiple sclerosis & Neuritis |
| Prednisolone | Multiple sclerosis & Neurosarcoidosis |
| Prednisone | Multiple sclerosis & Neurosarcoidosis |
| Amantadine | Multiple sclerosis & Parkinson's disease |
| Methylprednisolone | Neuralgia |
| Desvenlafaxine | Neuralgia |
| Nortriptyline | Neuralgia |
| Doxorubicin | Neuroblastoma |
| Vincristine | Neuroblastoma |
| Albendazole | Neurocystecercosis |
| chloroquine phosphate | Neurosarcoidosis |
| Hydroxychloroquine | Neurosarcoidosis |

TABLE 1-continued

| DRUG (generic name) | DISORDER(S) |
|---|---|
| Infliximab | Neurosarcoidosis |
| Pentoxyfilline | Neurosarcoidosis |
| Thalidomide | Neurosarcoidosis |
| Apomorphine | Parkinson's disease |
| Belladonna | Parkinson's disease |
| Benztropine | Parkinson's disease |
| Biperiden | Parkinson's disease |
| Bromocriptine | Parkinson's disease |
| Carbidopa | Parkinson's disease |
| carbidopa/entacapone/levodopa | Parkinson's disease |
| carbidopa/levodopa | Parkinson's disease |
| Entacapone | Parkinson's disease |
| Levodopa | Parkinson's disease |
| pergolide mesylate | Parkinson's disease |
| Pramipexole | Parkinson's disease |
| Procyclidine | Parkinson's disease |
| Rasagiline | Parkinson's disease |
| Ropinirole | Parkinson's disease |
| Rotiotine | Parkinson's disease |
| Scopolamine | Parkinson's disease |
| Tolcapone | Parkinson's disease |
| Trihexyphenidyl | Parkinson's disease |
| Seleginline | Parkinson's disease |
| Rivastigmine | Parkinson's disease & Alzheimer's disease |
| Anisindione | Thromboembolic stroke |
| Warfarin | Thromboembolic stroke |
| 5-hydroxytryptophan | Depression & Anxiety & ADHD |
| Duloxetine | Depression & Anxiety & Bipolar disorder |
| Escitalopram | Depression & Anxiety & Bipolar disorder |
| Venlafaxine | Depression & Anxiety & Bipolar disorder & Autism & Social anxiety disorder |
| Desvenlafaxine | Depression & Anxiety & PTSD & ADHD |
| Paroxetine | Depression & Anxiety & PTSD & Social anxiety disorder |
| fluoxetine/olanzapine | Depression & Bipolar disorder |
| l-methylfolate | Depression & BPD |
| Amitriptyline | Depression & PTSD |
| Sertraline | Depression & PTSD & Bipolar disorder & Social anxiety disorder |
| Fluvoxamine | Depression & PTSD & Social anxiety disorder |
| Olanzapine | Depression & Schizophrenia & Bipolar disorder |
| Paliperidone | Depression & Schizophrenia & Bipolar disorder |
| Aripiprazole | Depression & Schizophrenia & Bipolar disorder & Autism |
| Quetiapine | Depression & Schizophrenia & PTSD & BPD & Bipolar disorder |
| Risperidone | Depression & Schizophrenia & PTSD & BPD & Bipolar disorder & Autism |
| Amisulpride | Depression & Social anxiety disorder |
| Chlorpromazine | Psychosis |
| Droperidol | Psychosis |
| Fluphenazine | Psychosis |
| Periciazine | Psychosis |
| Perphenazine | Psychosis |
| Thiothixene | Psychosis |
| Triflupromazine | Psychosis |
| Haloperidol | Psychosis & Dementia |
| Prazosin | PTSD |
| Clozapine | Schizophrenia |
| Flupenthixol | Schizophrenia |
| Iloperidone | Schizophrenia |
| Loxapine | Schizophrenia |
| Mesoridazine | Schizophrenia |
| Promazine | Schizophrenia |
| Reserpine | Schizophrenia |
| Thioridazein | Schizophrenia |
| Zuclopenthixol | Schizophrenia |
| Asenapine | Schizophrenia & Bipolar disorder |
| Levomepromazine | Schizophrenia & Bipolar disorder |
| Ziprasidone | Schizophrenia & Bipolar disorder |
| Molindone | Schizophrenia & Psychosis |
| Pimozide | Schizophrenia & Psychosis |
| Thioridazine | Schizophrenia & Psychosis |
| Cytarabine | Chemotherapy, hematological malignancies |

According to some embodiments, the infusate is delivered to a patient at an infusion rate in the range of from about 1 to 3 μL/minute.

As discussed herein, insertion of the surgical cannula 100 (or any other surgical, e.g., delivery, cannula) can be tracked in near real time by reference to a void in the patient tissue caused by the cannula 100 and reflected in the MR image. In some embodiments, one or more MRI-visible fiducial markers may be provided on the surgical cannula 100, MR scanned and processed, and displayed on the UI. In some embodiments, the surgical cannula 100 may itself be formed of an MRI-visible material, MR scanned and processed, and displayed on the UI.

According to some embodiments, the surgical cannula may include an embedded intrabody MRI antenna that is configured to pick-up MRI signals in local tissue during an MRI procedure. The MRI antenna can be configured to reside on a distal end portion of the surgical cannula. In some embodiments, the antenna has a focal length or signal-receiving length of between about 1-5 cm, and typically is configured to have a viewing length to receive MRI signals from local tissue of between about 1-2.5 cm. The MRI antenna can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. 2003/0050557; 2004/0046557; and 2003/0028095, the contents of which are also hereby incorporated by reference as if recited in full herein.

While the surgical cannula 100 and needle 120 have been identified herein as delivery devices and methods for delivering a substance to a patient have been described, in accordance with some embodiments of the invention, the cannula 100 and needle 120 and associated methods can be used to withdraw a substance (e.g., spinal fluid) from a patient. Thus, it will be appreciated that the devices and methods as disclosed herein can be used to transfer a substance into and/or from a patient.

While the devices have been described herein primarily with reference to MRI-guided insertion and infusion procedures, in some embodiments the devices can be used in procedures without MRI guidance.

While the surgical cannula 100 has been described in use with a trajectory guide 50b, the cannula may be used with other types of trajectory guidance or stereotactic frames or without a stereotactic frame or trajectory guide.

The devices as depicted in may typically be employed for acute treatments. However, the systems, cannula, methods and procedures described herein may likewise be used for installation of a chronic delivery cannula or catheter. Chronic systems may be installed in the same manner as the acute systems 10 (FIG. 1) except that the delivery needle 120 or portion thereof can be configured to remain in the patient post-first delivery and connect to a port device installed on the patient (e.g., behind the patient's ear) to provide an (external) access point for subsequently releasably coupling the connection tubing 140. The pump P can be periodically or continuously connected to the needle 120 to deliver a therapeutic substance to a target region of the patient. In some embodiments, the connecting tubing, the pump and a substance reservoir may be implanted in the patient and connected to the infusion needle 120 by the tubing so that the port device s not needed, similar to an IPG and electrical stimulation lead. The chronic system can allow delivery of the substance or substances at different delivery times without requiring another surgical implantation procedure.

The system 10 may also include a decoupling/tuning circuit that allows the system to cooperate with an MRI scanner 20 and filters and the like. See, e.g., U.S. Pat. Nos. 6,701,176; 6,904,307 and U.S. Patent Application Publication No. 2003/0050557, the contents of which are hereby incorporated by reference as if recited in full herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A surgical device for transferring fluid to or from a subject, comprising:
   an elongate guide cannula having opposing proximal and distal ends with an open axially extending lumen, wherein the proximal end comprises a guide cannula connector; and
   an elongate needle having a length with opposing proximal and distal ends extending between an intrabody segment and an external segment of the needle, wherein the needle comprises a needle-cannula connector that is configured to attach to the guide cannula connector above the intrabody segment, wherein at least a major portion of the external segment of the needle resides in a length of flexible tubing, and wherein the elongate needle is configured to be slidably inserted into the guide cannula lumen so that the distal end of the needle extends out of the distal end of the guide cannula.

2. The device of claim 1, wherein the elongate needle comprises fused silica glass and the distal end of the needle has a stepped configuration with a first segment having a first outer diameter that merges into a second end segment having a second smaller outer diameter, the second segment having a length that extends to a tip of the needle, and wherein the needle extends out of the guide cannula a distance between about 2 mm to about 30 mm.

3. The device of claim 1, wherein the needle-cannula connector releasably attaches to the guide cannula connector, and wherein the flexible tubing is attached to a proximal end portion of the needle-cannula connector and extends above the needle-cannula connector to encase a length of about 4-10 feet of the external segment of the needle therein.

4. The device claim 1, further comprising an elongate stylet having opposing proximal and distal ends, the distal end having a sharp tip and the proximal end comprising a stylet connector that releasably attaches to the guide cannula connector, wherein the stylet has a body that is slidably receivable in the cannula lumen.

5. The device of claim 1, wherein the needle is a fused silica glass needle, wherein the external segment of the needle comprises a portion that extends above the needle-cannula connector and this portion has a length in a range of about 4-10 feet, and wherein at least a major portion of the needle above the needle-cannula connector resides inside the flexible tubing.

6. The device of claim 1, further comprising a depth stop with an open lumen, the depth stop configured to reside directly on an outer surface of the elongate guide cannula at an upper to mid portion of the guide cannula with the guide cannula extending through the open lumen of the depth stop.

7. The device of claim 1, wherein the elongate guide cannula comprises a ceramic material.

8. The device of claim 1, wherein the elongate guide cannula has an outer polymeric coating and/or sleeve, and wherein the distal end of the guide cannula is tapered so that it has a smaller outer diameter at a tip relative to an outer diameter of the guide cannula rearward of the tip.

9. The device of claim 1, wherein the elongate needle is an infusate needle and has a stepped distal end configuration and is integrally attached to the flexible tubing as a subassembly, wherein the device further comprises a metal elongate stylet with a sharp tip on a distal end and a stylet connector on a proximal end, wherein the stylet and needle are releasably interchangeably attachable to the guide cannula connector, and wherein the needle, stylet and guide cannula are all MRI compatible for use in an MRI guided procedure.

10. An MRI compatible intrabody fluid transfer device for transferring a substance to and/or from a patient, comprising:
a rigid tubular guide cannula having an open lumen extending therethrough with a guide cannula connector on a proximal end thereof;
a needle having a length with an external segment and an intrabody segment, wherein the needle has a distal end portion, and wherein the needle is configured to be slidably insertable into the rigid guide cannula so that the needle connector attaches to the guide cannula connector and the distal end portion of the needle extends beyond a distal end of the tubular guide cannula;
a needle connector attached to the needle above the intrabody segment configured to releasably couple to the guide cannula connector; and
flexible tubing that encases about 4-10 feet of the external segment of the needle above the needle connector.

11. The device of claim 10, further comprising a metal stylet with a stylet connector configured to releasably interchangeably attach to the guide cannula connector in place of the needle with the needle connector.

12. The device of claim 11, wherein the guide cannula has an exterior surface on a distal end portion thereof that tapers down in size to a tip thereof to define a third coaxially disposed stepped segment that resides a distance rearward of the first and second segments and has a larger outer diameter than both the first and second segments.

13. The device of claim 10, wherein the tubular guide cannula comprises a ceramic material.

14. The device of claim 10, wherein the tubular guide cannula has an outer polymeric coating and/or sleeve.

15. The device of claim 10, wherein the distal end of the tubular guide cannula is tapered so that it has a smaller outer diameter at a tip relative to an outer diameter of the guide cannula rearward of the distal end.

16. The device of claim 10, wherein the tubular guide cannula comprises a ceramic material and a conformal outer polymeric sleeve.

17. The device of claim 10, wherein the distal end portion of the needle that extends out of the tubular guide cannula has at least first and second segments that are co-axially disposed with different outer diameters, with a smallest sized outer diameter of the first segment extending to a tip thereof.

18. The device of claim 17, wherein the first smallest outer diameter segment has a longitudinal length of between about 1 mm to about 10 mm, wherein the second segment has a longitudinal length of between about 2 mm to about 20 mm, and wherein a distal tip of the guide cannula resides a distance between 3 mm to about 30 mm from a distal tip of the needle.

19. The device of claim 10, wherein the needle has a fused glass silica body with a single continuous lumen with at least a major portion above the needle-connector of residing inside the flexible tubing, wherein the needle comprises a portion with an exposed length of the fused glass silica body that is not encased in the flexible tubing and that extends below the needle connector and has a lesser length than the length in the flexible tubing.

20. The device of claim 10, wherein an outer surface of the tubular guide cannula has a size and geometry adapted for use with a stereotactic frame, and wherein the needle has an inner diameter of between about 100 µm to about 750 µm.

21. The device of claim 10, further comprising a trajectory guide holding the guide cannula, wherein the intrabody length segment is less than the external length segment of the needle, and wherein the needle-cannula connector engages the guide cannula connector a distance above the trajectory guide.

22. A method of transferring a substance to and/or from a patient, the method comprising:
providing a guide cannula with an axially extending interior lumen;
inserting a stylet with a sharp distal tip into the guide cannula lumen and attaching the stylet to the guide cannula so that the distal tip extends a distance outside the guide cannula distal end;
placing the attached guide cannula and stylet into a trajectory guide of a stereotactic frame; then
introducing the guide cannula and stylet into a subject so that the distal end of the guide cannula resides proximate a target site; then
slidably withdrawing the stylet from the guide cannula and out of the subject, while leaving the guide cannula in position; then
inserting a needle having an internal lumen into the guide cannula lumen and attaching a needle connector to the guide cannula, wherein a distal end of the needle can slidably extend out of a distal end of the guide cannula and reside at the target site, wherein an external length segment of the needle extends above the needle connector encased in flexible tubing; then
transferring the substance to or from the target site through the needle lumen.

23. The method of claim 22, wherein the needle is an infusion needle, wherein the transferring the substance to or from the target site is carried out by infusing a substance, and wherein the needle has a length in a range of 4-10 feet and at least a major portion of the external length segment is encased in the flexible tubing while the distal end of the needle is exposed and unencased in the flexible tubing.

24. An MRI compatible infusion needle for transferring a substance to and/or from a patient, the needle comprising:
an elongate fused silica needle body attached to a needle-guide cannula connector that is adapted to connect to a guide cannula, the connector residing spaced apart from a distal end of the needle, wherein the needle body has an intrabody length segment and an external length segment, wherein the external length segment is in a range of about 4-10 feet and is encased in flexible tubing, wherein the intrabody length segment extends a distance below the flexible tubing and below the needle-guide cannula connector, and wherein an exterior surface of the distal end of the needle is outside the flexible tubing and has at least first and second co-axially disposed segments having different outer diameters.

\* \* \* \* \*